(12) United States Patent
Fitch et al.

(10) Patent No.: US 11,607,255 B2
(45) Date of Patent: Mar. 21, 2023

(54) METHOD AND APPARATUS FOR TREATING CRANIAL CRUCIATE LIGAMENT DISEASE IN CANINES

(71) Applicants: Randall Fitch, Pleasanton, CA (US); Robert Von Zabern, Riverside, CA (US)

(72) Inventors: Randall Fitch, Pleasanton, CA (US); Robert Von Zabern, Riverside, CA (US)

( * ) Notice: Subject to any disclaimer, the term of this patent is extended or adjusted under 35 U.S.C. 154(b) by 27 days.

(21) Appl. No.: 16/549,932

(22) Filed: Aug. 23, 2019

(65) Prior Publication Data

US 2021/0052311 A1 Feb. 25, 2021

(51) Int. Cl.
| | | |
|---|---|---|
| A61B 17/80 | (2006.01) | |
| A61F 2/08 | (2006.01) | |
| A61B 17/15 | (2006.01) | |
| A61B 17/17 | (2006.01) | |
| A61D 1/00 | (2006.01) | |
| A61F 2/30 | (2006.01) | |

(52) U.S. Cl.
CPC ........ *A61B 17/8095* (2013.01); *A61B 17/151* (2013.01); *A61B 17/157* (2013.01); *A61B 17/1767* (2013.01); *A61D 1/00* (2013.01); *A61F 2/0805* (2013.01); *A61F 2/0811* (2013.01); *A61F 2002/0882* (2013.01); *A61F 2002/307* (2013.01)

(58) Field of Classification Search
CPC . A61B 17/8095; A61B 17/151; A61B 17/152; A61B 17/157; A61B 17/1675; A61B 17/1764; A61B 17/808; A61B 17/1728
USPC .................................................... 606/86 B
See application file for complete search history.

(56) References Cited

U.S. PATENT DOCUMENTS

| | | | | |
|---|---|---|---|---|
| 4,409,973 A | * | 10/1983 | Neufeld | A61B 17/1637 606/178 |
| 9,427,240 B2 | | 8/2016 | Von Zabern | |
| 2013/0338781 A1 | * | 12/2013 | Bordeaux | A61F 2/30724 623/20.16 |
| 2014/0288562 A1 | * | 9/2014 | Von Zabern | A61B 17/1637 606/88 |
| 2015/0018888 A1 | * | 1/2015 | Geebelen | A61B 17/56 700/98 |
| 2018/0325568 A1 | * | 11/2018 | Wotton | A61B 17/8057 |
| 2019/0262045 A1 | * | 8/2019 | Garino | A61B 17/8866 |

\* cited by examiner

*Primary Examiner* — Matthew J Lawson
(74) *Attorney, Agent, or Firm* — Marcus C. Dawes

(57) ABSTRACT

A surgical guidance system (SGS) for performing a cruciate pivot osteotomy in canines to treat cranial cruciate ligament disease. The SGS comprises a guide, a jig, and a plate. The guide is first placed over the tibia until it interacts with specific anatomical features of the tibia, thereby marking the proper position for the jig to be placed. After the jig has been secured, a blade defines an osteotomy within a proximal portion of the tibia. A portion of the jig is then cranially rotated providing a rotational correction of the proximal tibia. A compressive force is then applied to the osteotomy by the jig. Next the multiplane locking plate is placed over the osteotomy as dictated by the features of the jig. After initially securing the plate into its correct position, the jig is removed and the plate is then secured to the cranial surface of the tibia.

20 Claims, 13 Drawing Sheets

METHOD AND APPARATUS FOR TREATING CRANIAL CRUCIATE LIGAMENT DISEASE IN CANINES

BACKGROUND

Field of the Technology

The invention relates to the field of surgical techniques for the treatment of cranial cruciate ligament disease in canines, specifically to surgical methods based on CORA-based leveling osteotomy.

Description of the Prior Art

Cranial cruciate ligament injury is the most prevalent orthopedic injury in the dog requiring surgical repair with estimates of $1.32 billion spent in the United States on the treatment of this condition in 2003 (Wilke VL, JAVMA 2005). In that same year, the average spent per patient was $1840 with a range of 0 to $5000. Treatment costs have continued to escalate to the current $3500-6500. Implant costs likely do not substantially influence medical costs as the only make-up ~3-5% of the total medical bill.

Biomechanically, the canine stifle or knee has many advantages over the human knee that one would expect to protect the stifle from injury. The dog's stifle is spared from the type of destructive hyperextension stresses that produce injuries in people and is not subjected to the same type of landing forces. In addition, the dog's knee geometry limits extension further protecting it (15 degrees of flexion is full extension with normal standing angles of 35 degrees of flexion). Therefore coupling hyperextension with high impact, a common mode of knee injury in humans, is nearly impossible in the dog. Yet, the prevalence of cruciate ligament disease appears to be greater in dogs than humans which is further surprising when you consider that 60% of weight-bearing is distributed to the forelimbs of these quadrupeds.

An epiphany in the understanding of the biomechanics in the canine stifle occurred in the with the discovery interaction of the canine knee (stifle) with other joints in the limb and especially the tarsal joint. In particular, the canine stifle does not work independently but is part of a larger mechanism. One subset of this mechanism demonstrates that as the stifle extends, the lower limb is propelled. Specifically, as the tarsus extends and the tarsophalangial joints flexes producing propulsion. This same mechanism is responsible for producing enhanced propulsion which resulting on increased loading (Henderson 1978). Through this mechanism, it was realized that normal weight-bearing forces were magnified within the stifle joint subjecting the cranial cruciate ligament to a magnified load.

Quite different from humans, this mechanism is quite evident by the elevation of the heel of the dog (the calcaneus) which is not in contact with the ground. Biomechanically, elevation of the heel transforms the lower foot (phalanges through the calcaneus) into a loaded lever. Weight-bearing forces transferred through the toes are then magnified across the long foot.

The gastrocnemius tendon transfers this tensional force through its origin on the caudal aspect of the femur producing magnified compression of the tibia. The femoral condyles articulate with the slanted tibial plateau (about 25 degrees on average) producing constant load constrained by the cranial cruciate ligament. Weight-bearing increases this shear force through the described lever mechanism which continually places the cranial cruciate ligament or any repair under tension. The shear force to which the cranial cruciate ligament is subjected can be altered by adjusting the tibial slope, which is the foundation of the tibial plateau leveling osteotomy (TPLO).

Another force of consideration in the canine stifle is the tensional force of the quadriceps mechanism. This force places additional load on to the cranial cruciate ligament proportional to the angle of the patella tendon tension in relation to the joint surface. Therefore, if the patella tendon tension is oriented obliquely to the joint surface, additional shear force is produced within the joint contributing to cranial cruciate ligament stress.

When the patella tendon tensional force is oriented more parallel to the direction of the cranial cruciate ligament, this has a load sparing effect. Diminishing stress on the cranial cruciate ligament can be achieved by changing the orientation of the patella tendon. Anatomically this is achieved by rotating and cranially displacing the tibial tuberosity which is the insertion point of the quadriceps.

Reorientation of both the quadriceps and gastrocnemius tension diminishes cranial cruciate ligament shear stress through both concentrated quadriceps tension and gastrocnemius tension components of the gait cycle, thereby providing more comprehensive stability for the propulsion and swing phases of the gait cycle. This can be achieved through tilting the complete intact tibial epiphysis resulting in reorientation of both components and is the concept of the CBLO.

The additional weight-bearing shear forces produced in the stifle are paramount to understanding the pathogenesis and progression of cranial cruciate ligament tears as well as the potential mechanisms for repair. Due to the continual stress that the cranial cruciate ligament is subjected to with weight bearing, even a small tear of the cranial cruciate ligament propagates over time with continued weight-bearing. The cranial cruciate ligament has poor vascularity within this intra-articular environment with minimal healing capacity. Repetitive strain therefore produces accumulating non-healing ligament fiber injuries increasing laxity resulting in even greater ligament strain cascading to complete ligament failure over time.

Traditionally, surgical repair techniques focused on functionally replacing the ruptured cranial cruciate ligament with limited success in dogs. This is likely due in part to the unaccounted magnified continuous stress placed on the ligament repair during weight-bearing not present in humans. The high prevalence of bilateral cranial cruciate ligament tears in dogs further support an underlying architectural contribution to ligament stress. A conceptional change occurred in the approach to surgical intervention regarding this condition thirty years ago which centered on altering the regional osseous architecture to reduce articular shear force produced through weight-bearing.

Many techniques were developed that altered the underlying osseous geometry to diminish weight-bearing shear forces in the stifle. The tibial plateau leveling osteotomy (TPLO) was reported in 1993 in which the tibial plateau articular surface was rotated to eliminate tibial thrust in the stifle joint generated through the gastrocnemius mechanism (Slocum 1993). Additionally, other techniques were developed to alter the underlying osseous anatomy of the tibia by either (1) altering the tibial plateau angle or (2) altering the tensional angle of the patella tendon (for example, tibial tuberosity advancement). In the tibial tuberosity advancement (TTA), the patella tendon orientation is altered by cranially displacing the tibial tuberosity (the insertion of the patella tendon) through a surgical osteotomy distracted with a metallic spacer. It is estimated that more than 70,000 tibial tuberosity advancement (TTA) procedures have been performed to date. TTA seeks to control cranial tibial subluxation via elimination of cranial tibial thrust by orienting the patellar tendon angle (PTA) to a more parallel orientation with the cranial cruciate ligament during the weight-bearing phase of the gait.

Both of these prior techniques are very prevalent and commonly performed with a high success rate and clinical benefit. However, all of these surgical techniques address only one component of tensional stress placed on the stifle not providing stability through the full gait cycle. Second look arthroscopic evaluation of stifles treated with TPLO demonstrated a progression of articular erosions suggesting joint laxity with cartilage shearing persists (Hulse, Beale, Kerwin 2010, Matis ACVS Proceedings 2005). Also the TTA has been fraught with a high rate of meniscal injury indicating ongoing instability. In addition, these surgical techniques result in intra-articular disruption with displacement of articular structures. Both TPLO and TTA have displacement limitation due to the severe intra-articular displacement produced so that patients with severe angulation cannot be completely corrected with these surgical techniques. The complications and limitations associated with all of these surgical procedures necessitates the search for a better surgical solution.

In 2010, Donald Hulse, DVM, DACVS, DECVS, first described an adjustable crescentic osteotomy of the proximal tibia that provides more comprehensive stability addressing quadriceps and gastrocnemius tensional forces. He described this as a CORA based leveling osteotomy (CBLO) in that the osteotomy was centered at the maximum point of curvature of the proximal tibia. The concept of CORA (Centre of Rotation of Angulation) is extrapolated from Dr. Dror Paley's work in human orthopedic limb alignment. The CORA is the geometric center of curvature within a bone. Through this surgical methodology anatomic and mechanical axes can be realigned through specifically planned rotational osteotomies. In essence, the weight-bearing forces are realigned through the center of the joint and perpendicular to the articular joint surfaces eliminating destructive shear force. As applied to the stifle, the mechanical axis of the stifle is realigned with the anatomic axis down the center of the tibia to neutralize shear forces during weight-bearing. Therefore, weight-bearing forces are both realigned perpendicular to the joint surfaces and through the center of the tibia.

CORA based osteotomies have several advantages over other osteotomy techniques such closing wedge, opening wedge, transverse, and the like. Tibial length is minimally altered with CORA based rotational osteotomy. Preservation of tibial length diminishes fibula stress or abnormal canting (mediolateral malalignment) of the tibial plateau resulting in varus or valgus deformity. Closing wedge osteotomies of the tibia provide a wedge-shaped ostectomy of the tibia (Wallace VCOT 2011). However, the closing wedge ostectomy decreases tibial length which due to preservation of the fibula length producing angulation at the joint altering gait. Angular deformity producing "pivot shift" has been noted in TPLO patients possibly attributed to malalignment in which abnormal rotational is produced with weight-bearing. Ultimately the CORA based approach provides controllable sagittal and frontal alignment of the mechanical and anatomic axes.

Open, closing, and TPLO osteotomies produce displacement that not only alters limb length, but can also produce impingement of regional structures. The TPLO rotational osteotomy produces intra-articular and caudal tibial cortical acute displacement of regional tissues with possible impingement of theses tissues (popliteus, gastrocnemius, peroneal nerve caudal to the tibia or patella tendon, femoral condyles, menisci at the joint). In addition, other articular structures such as the patella tendon are not placed in jeopardy during the osteotomy and no secondary patella tendon enlargement (patellar tendonitis) is noted.

Minimizing joint invasion and alteration is important. An increased incidence of osteoarthritis has been noted with intra-articular procedures in the dog (Matis ACVS Proceedings 2005). A prior study (Jandi As, Schulman AJ Vet Surg 2007) showed that the loss of range in motion can occur with TPLO. In fact the reported loss of knee range of motion in humans is 4-35% (Millett Am J Sports Me 1999 and 2001). Stifle arthrosis especially of the cranial femorotibial joint impacts joint range of motion and clinical function.

What is needed therefore is a surgical treatment of cranial cruciate ligament disease which minimizes bone displacement, thus minimizing impact to the joint and regional tendons, ligaments, joint capsule, muscles and nerves. Additionally, patella tendon desmitis as noted with TPLO should be avoided. The treatment should also provide an especially attractive alternative to prior procedures in that it should allow for realignment of mechanical forces and articular shear forces within the stifle so as to prevent progression of further cranial cruciate ligament tearing. The treatment should also be performed without invasion of the joint or risk of any further injury to the joint and cranial cruciate ligament that occurs with any joint invasion. Development and evolution of a reliable, superior surgical technique with simplified application would provide marked positive impact for our pet population.

BRIEF SUMMARY

The current invention provides balanced permanent stability for canines with cruciate ligament injuries combining the best corrective principles of modern surgical techniques. Joint instability is eliminated through realignment of the joint surfaces with no articular disruption preserving normal joint motion.

The current invention is a Surgical Guidance System (SGS) which is used to perform a cruciate pivot osteotomy so as to provide precise control with exact orientation and rotation. Using the SGS to perform the cruciate pivot osteotomy results in no articular surface disruption and no significant cortical surface displacement or large anatomic displacement.

A crescentic osteotomy is first provided with cannulated bi-radial blade which provides a three-dimensional controlled osteotomy for exact compression, apposition, and accelerated healing. The cruciate pivot osteotomy is a CORA based leveling osteotomy in which the entire proximal tibial epiphysis is rotated intact without articular invasion or disruption of the tibial plateau. The osteotomy is placed distal to the joint avoiding peri-articular structures and intra-articular invasion. Translation at the osteotomy is controllable and can be minimized with adjustments in the radius and position of the osteotomy. This translates into no articular displacement and minimal displacement at the cortical surface thereby resulting in minimal muscle, tendon, nerve or vascular impingement.

The cruciate pivot osteotomy produces a nearly 180 degree arc in the tibia. This provides several advantages over previously used procedures including adjustability and greater stability. The cruciate pivot osteotomy may provide advantages in many special clinical situations such as excessive tibial slope and partial cranial cruciate ligament ruptures. Patients with angular deformity such as excessive tibial slope can be fully corrected with only one osteotomy not requiring additional osteotomies with high complications as required with other techniques. The SGS of the current invention provides specific intra-operational real time preplanning, specific and precise osteotomy placement and orientation, rotational measurement, osteotomy three-dimensional compression, retention of post-rotational orientation for implant placement and implant placement guidance.

The current SGS provides compression of the osteotomy, specifically with bi-radial blade technology converts displacement to circumferential compression at the osteotomy. The SGS also provides exact rotation without the need of a rotation chart. Additionally, the SGS of the current invention provides advantages over traditional CBLO eliminating the need of a trans-osteotomy screw. The osteotomy is precisely guided and provides exact three-dimensional osteotomy placement and orientation. Other systems used in the art are non-guided and are thus "free-handed" which produces inconsistent and imprecise osteotomies.

The SGS also comprises a specifically designed titanium implant for post rotational stabilization which is low contact, multi-planar and locking. Although the implant provides sophisticated customized mechanical support, it is also very simple to place when guided by the surgical guidance system of the current invention. The current invention does not require depth gauge measurements and eliminated biofilm formation from repetitive autoclaving since only new implants are placed.

Performing a cruciate pivot osteotomy using the SGS results in weight-bearing forces being aligned with the anatomic axis of tibia, thereby providing ideal stifle stabilization. Stifle stabilization is provided through a greater range of motion of the limb cycle including propulsion and swing phase without post-surgical articular erosion associated with performing TPLO. Furthermore, plate fixation does not require precise screw length measurement as the plate is stabilized by multi-planar fixation. The current invention does not require additional implant inventory, organization of implants, post-surgical cleaning and sterilization of unused implants thereby simplifying inventory and markedly decreasing costs.

Performing a cruciate pivot osteotomy permanently corrects joint architecture thus eliminating painful abnormal instability that occurs during weight bearing. Surgical rotation of the tibial joint surface through an adjustable curved osteotomy neutralizes shear stress and provides lifetime knee stability. A minimally reactive multi-planar titanium implant then rigidly stabilizes the osteotomy while it heals allowing for immediate weight bearing leading to fast and reliable recoveries. A hallmark advantage of a surgery performed by the SGS of the current invention is minimal joint interference allowing for free stifle motion since no implants cross the joint. Immediate rigid stability facilitates reliable bone healing with accelerated bony bridging of the osteotomy. Early weight bearing of the limb in turn leads to accelerated rebuilding of muscle mass and strength.

The current invention provides a method for treating cruciate ligament disease. The method includes determining an insertion position on a tibia with a guide, inserting a centering pin at the determined insertion position on the tibia and then disposing a jig onto the tibia. Next, an osteotomy is defined in the tibia followed by a proximal portion of the tibia being rotated. The proximal portion of the tibia is then secured into a post-rotational position, followed by the disposition of a plate in a position over the osteotomy as determined by a frame of the jig.

In one particular embodiment, the method step of determining the insertion position on the tibia for a centering pin with the guide includes disposing a first positioning peg coupled the guide adjacent to a cranial surface of the tibia and then disposing a second positioning peg coupled on the guide adjacent a caudal surface of the tibia. Disposing the first and second positioning pegs adjacent to the cranial and caudal surfaces of the tibia respectively also automatically centers a notch defined within the guide over the insertion position on the tibia for the centering pin.

In another embodiment, the method step of disposing the jig over the tibia includes aligning at least one joint probe coupled to the jig with at least one anatomical feature of the tibia.

In yet another embodiment, the step of disposing the jig over the tibia specifically includes disposing a lower arm rotationally coupled to the jig over the length of a distal portion of the tibia and then locking the lower arm into a fixed position relative to the jig and to the distal portion of the tibia. Additionally, locking the lower arm into a fixed position may further include aligning a plurality of feet disposed on the lower arm with a cranial and a caudal surface of the distal portion of the tibia.

In another embodiment, disposing the plate in a position over the osteotomy as determined by the position of the jig relative to the tibia includes inserting the plate within a center of a frame of the jig.

In a related embodiment, disposing the plate in a position over the osteotomy as determined by the position of the jig relative to the tibia includes disposing at least two cranial arms of the plate on a cranial surface of the tibia. In this embodiment, disposing at least two cranial arms of the plate on a cranial surface of the tibia may also further include disposing one of the at least two cranial arms of the plate on a proximal cranial surface of the tibia and disposing one of the at least two cranial arms of the plate on a distal cranial surface of the tibia.

In another embodiment, the step of rotating the proximal portion of the tibia includes rotating the proximal portion of the tibia through a rotation angle defined between a plurality of adjustable track guides disposed within the jig. Additionally, rotating the proximal portion of the tibia through a rotation angle defined between a plurality of adjustable track guides disposed within the jig itself includes sliding a rotation handle adjustably coupled to the jig through an angular track defined within the jig until contacting at least one of the plurality of track guides. Next, the plate may be aligned with the rotation handle after it has made contact with the at least one of the plurality of track guides.

In a further embodiment, disposing the jig onto the tibia includes aligning a concave surface of the jig with a corresponding convex surface of a proximal portion of the tibia.

In yet another embodiment, determining the insertion position on a tibia with the guide further includes obtaining a visual indication of the position of an osteotomy to be defined in the tibia.

The current invention also provides a system for treating cruciate ligament disease. The system includes a guide, an adjustable jig, and a plate which is configured to fit within a frame of the jig and onto a tibia. The jig specifically includes at least one joint probe configured to interact with the anatomical features of the tibia.

In one embodiment, the guide of the system includes a plurality of positioning pegs which are configured to interact with a cranial surface and a caudal surface of the tibia, respectively. The guide may also include a notch which is defined between the plurality of positioning pegs.

In another embodiment, the jig of the system includes a lower arm that is rotationally coupled to a frame of the jig and which is configured to extend down a length of a distal portion of the tibia. The lower arm further includes a plurality of feet that are disposed on a distal end of the lower arm. The plurality of feet are configured to contact a cranial surface and a caudal surface of the tibia, respectively.

In yet another embodiment, the plate of the system includes a plurality a cranial arms which are configured to extend from a medial surface of the tibia to a cranial surface of the tibia.

In a related embodiment, the jig of the system includes a track defined within a frame of the jig, a slidable rotation handle disposed within the track, and a track guide disposed within the track on either side of the rotation handle disposed within the track.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Figure 1A:
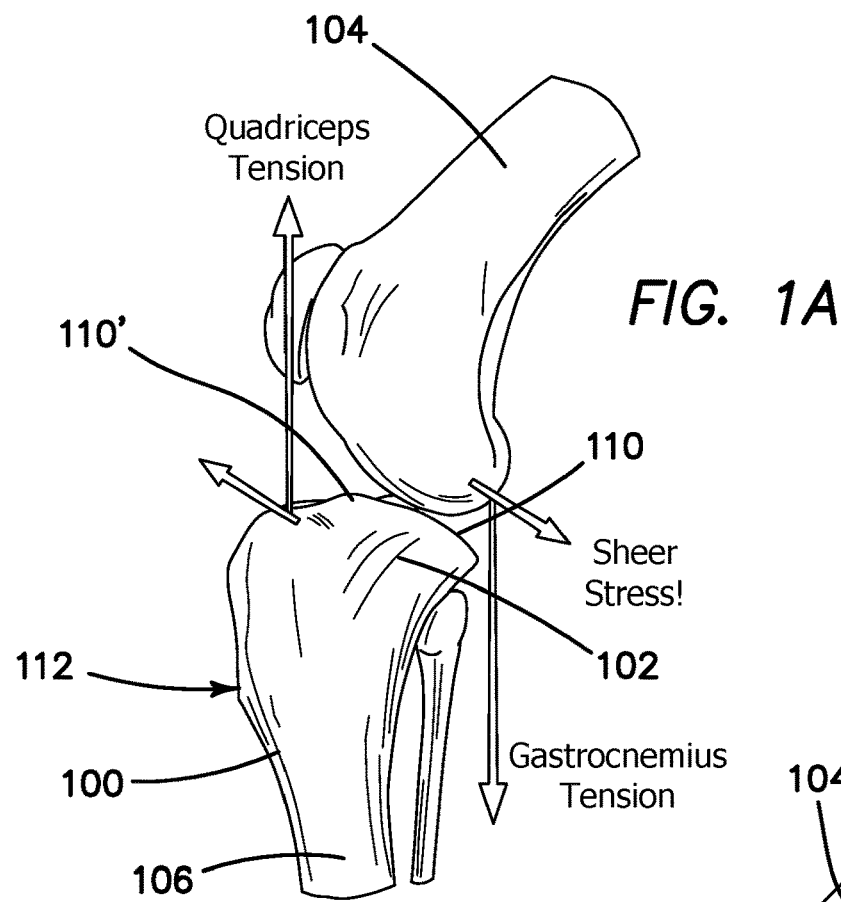
FIG. 1A is an illustration of a canine stifle before performing the cruciate pivot osteotomy of the current invention.
Figure 1B:
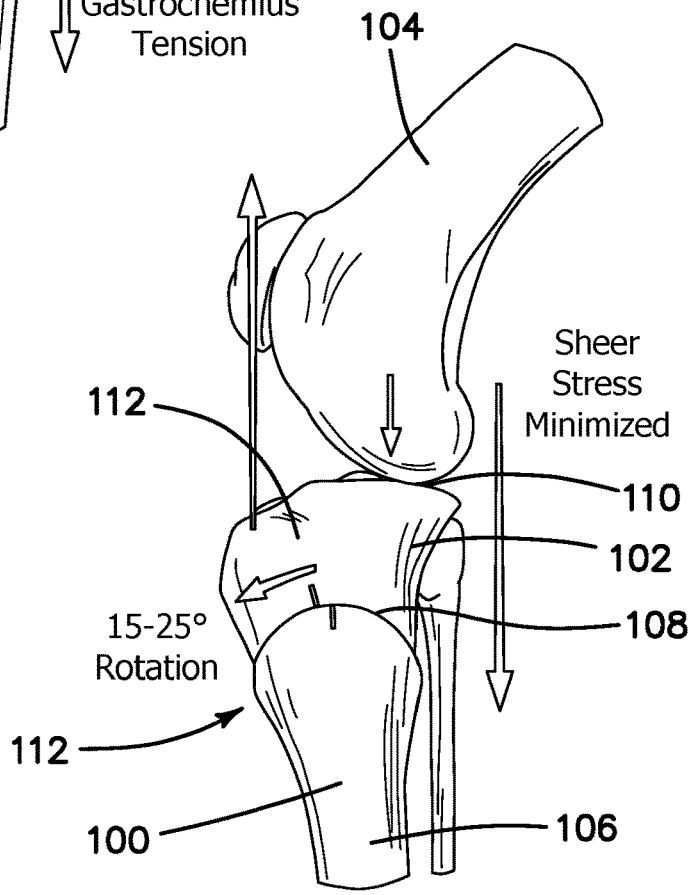
FIG. 1B is an illustration of a canine stifle after performing the cruciate pivot osteotomy of the current invention.

The current invention is a surgical guidance system (SGS) or kit 1 and a method for performing a cruciate pivot osteotomy, both of which are for surgically treating canine cranial cruciate ligament disease. FIGS. 1 and 1B are illustrations of a canine stifle comprising a tibia 100 and a femur 104 before and after performing a cruciate pivot osteotomy using the current SGS 1, respectively. The present invention provides a fast, accurate, and reliable means for performing an osteotomy 108 on the stifle of a canine, thereby allowing for a leveling of a proximal portion 102 of the tibia 100 relative to a distal portion 106 of the tibia 100. The current system and method further compresses the osteotomy 108 while providing an accurate template for a plate 80 which is then placed and affixed to the tibia 100 through a plurality of bone screws.

The current SGS 1 comprises a bi-planar geometry that will provide torsional stability when treating cranial cruciate ligament disease which was previously not possible using known CORA based leveling osteotomy (CBLO) techniques (Meyer 2016). The current system and method is easy and fast to place and does not require much contouring. The ability of the current invention to provide bi-planar support allows for the option of using unicortical screws which save additional time and cost over previously used CBLO or TPLO techniques. The current design also preserves the osteotomy reduction in three-dimensions and is easily adaptable to smaller canines, as the "dome shaped" osteotomy with a transosteotomy screw was very problematic for canines undergoing a CBLO or TPLO procedure.

To use the SGS 1 and begin the cruciate pivot osteotomy, the operated limb is first clipped from the inguinal region to below the tarsus using a number 40 blade. Surgical preparation is performed using chlorhexidine scrub and sterilely draped using a hanging-limb prep. The patient is slightly tilted toward the limb to allow the operated limb lay flat on the surgical table.

A standard medial surgical approach with exposure of the proximal tibia 102 is performed from the proximal patella to the mid tibia. This allows full visualization of the medial aspect of the stifle joint distally to allow for placement of a jig 20 and a multiplanar plate 80 as is further detailed below. Skin and subcutaneous tissues are retracted laterally. A standard medial approach is made with either arthroscopic evaluation of the stifle joint or medial arthrotomy for joint inspection and treatment. Cautery is utilized to make a small inverted "T" along the caudal aspect of the patella tendon to the tibial plateau 110. This allows exposure of the tibial plateau 100 caudal to the patella tendon and cranial to the medial collateral ligament. Note in FIG. 1A that that caudal slope of the tibial plateau 110 is typically angled steeply at a 45 degree angle relative the cranial portion of the tibial plateau 110. As is further described below, this will be the location for the joint probe 60 of a jig 20 to be placed, namely caudally where the articular surface flattens out. In addition, this will be the same location a cranial arm of a multiplanar plate 80 will be placed after the joint probe of the jig 20 has been removed.

Specific to the pivot osteotomy and placement of the multiplanar plate 80, exposure of the proximal tibia 102 is preferably performed by exposing the caudal aspect of the tibia at the level of the lower tibia tuberosity 112 by first cauterizing vertically near the caudal tibial surface and then sliding a large periosteal elevator to elevate the tissues from the caudal tibia surface. The periosteal elevator is then replaced with a Hohman retractor securing the handle with the surrounding drapes using an Allis forceps or similar instrument ("hands free technique"). Additionally, exposure of the cranial aspect of the tibial plateau 110 is achieved by cauterizing a line along the joint surface extending from just caudal to the patella tendon and following the tibial plateau 110 caudally for 8-10 mm. This will look like a slanted inverted "T" as the tibial plateau 110 slants proximal (110'). Finally, exposure of the proximal tibia 102 should also preferably elevate a small section of the cranial tibialis at the cranial aspect of the tibia 100 at the site of a fifth screw site to facilitate later placement of the multiplanar plate 80 as is detailed further below.

Next, a centering pin 22 is utilized to ensure controlled positioning and orientation of an osteotomy blade 52 and the resulting osteotomy 108. Exact positioning and centering of the osteotomy 108 as well as transverse orientation of the osteotomy 108 relative to the tibia 100 are essential for correct sagittal rotation of the tibial plateau 110. In order to place the centering pin 22 in the correct position, a guide 10 as seen in FIGS. 5-7 is used.

Figure 5:
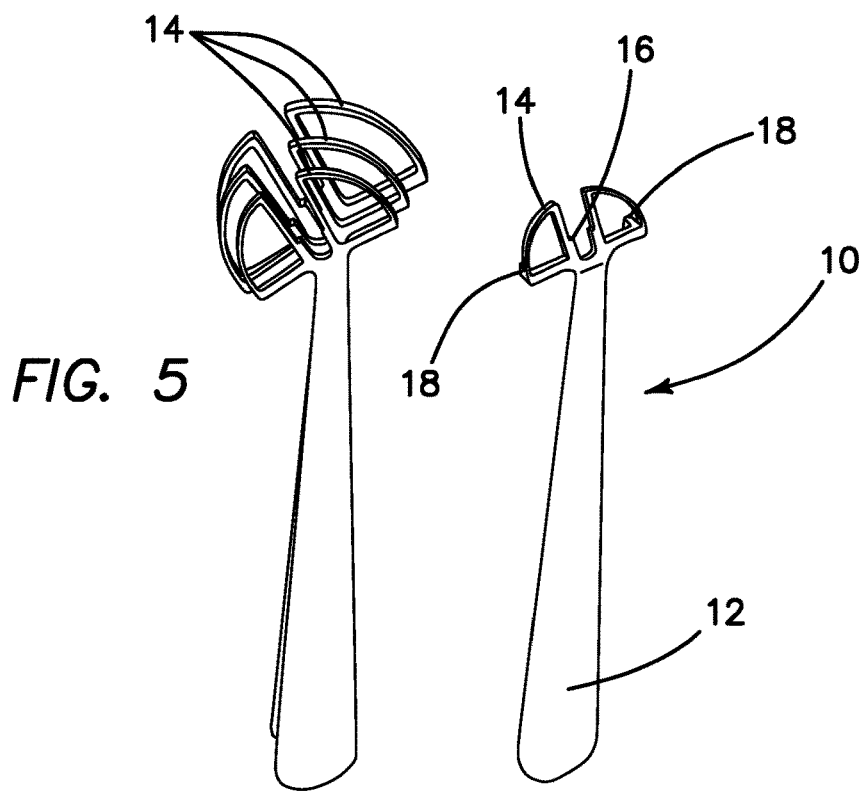
FIG. 5 is a top down view of a plurality of guides of the SGS used to perform the cruciate pivot osteotomy of the current invention.

The guide 10 is comprised of high quality stainless steel resistant to repeated autoclave sterilization and as seen in FIG. 5, is specifically sized to fit the tibia of a variety of different breeds. The guide 10 comprises a horizontal arc 14 disposed on a distal end of a handle 12. Defined in the center of the arc 14 is a notch 16 which forms a substantial "V" shape in the middle of the arc 14 and which provides an aperture for disposing the centering pin 22. Disposed on the respective cranial and caudal edges of the guide 10 are a pair of corresponding positioning pegs 18. The positioning pegs 18 on the cranial and caudal edges of the guide 10 facilitate the positioning and sizing of the template and determines the centering pin 22 placement.

Figure 6:
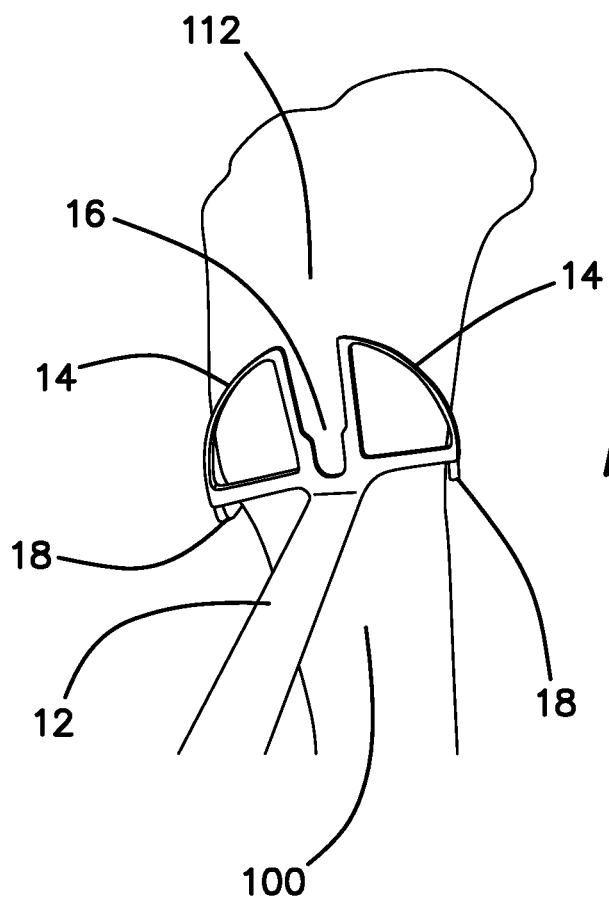
FIG. 6 is a top down view of one of the plurality of guides seen in FIG. 5 when placed over the tibia of a canine.
Figure 7:
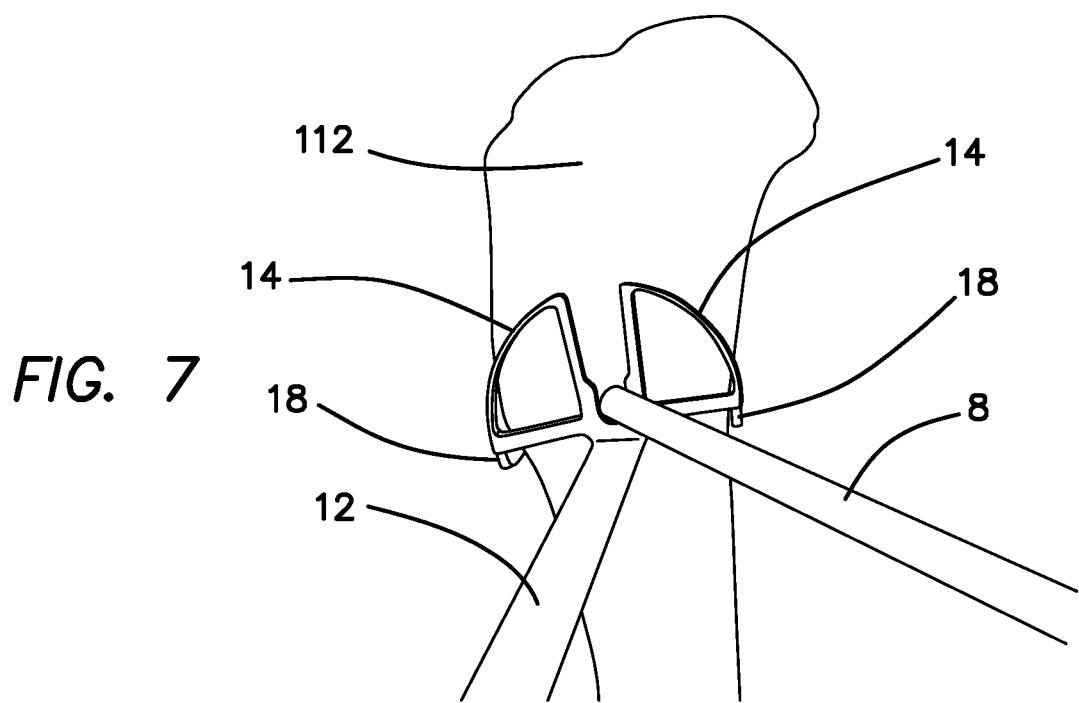
FIG. 7 is a top down view of the guide seen in FIG. 6 as a centering pin is being inserted into the tibia with a quick connect driver.

Specifically, the guide 10 is placed over the cranial and caudal surfaces of the tibia 100 as seen in FIG. 6 and slid proximally until it is stopped by the anatomical contours of the tibia 100, thereby automatically identifying and disposing the notch 16 at the center of the tibia 100. If the proper guide 10 has been selected for the breed or size of the canine currently being operated on, the guide 10 will specifically dispose the notch 16 near the lower tibial tuberosity 112 as seen in FIGS. 6 and 7. In addition to centering the notch 16 for placement of the centering pin 22, the arc 14 provides a visualization of the exact orientation and position of an osteotomy which would be made by a blade that is centered about the position of the notch 16. In this fashion, the user can use the guide 10 to quickly and easily identify and preplan the intended osteotomy placement within the tibia 100. Once the guide 10 is correctly placed, the centering pin 22 is disposed into the notch 16 by a power drill or quick connect driver 8 seen in FIG. 7. The handle 12 of the guide 10 is angled relative to the horizontal arc 14 so as to provide sufficient room for the user to operate the quick connect driver 8 and implant the centering pin 22 to the tibia 100.

Figure 2:
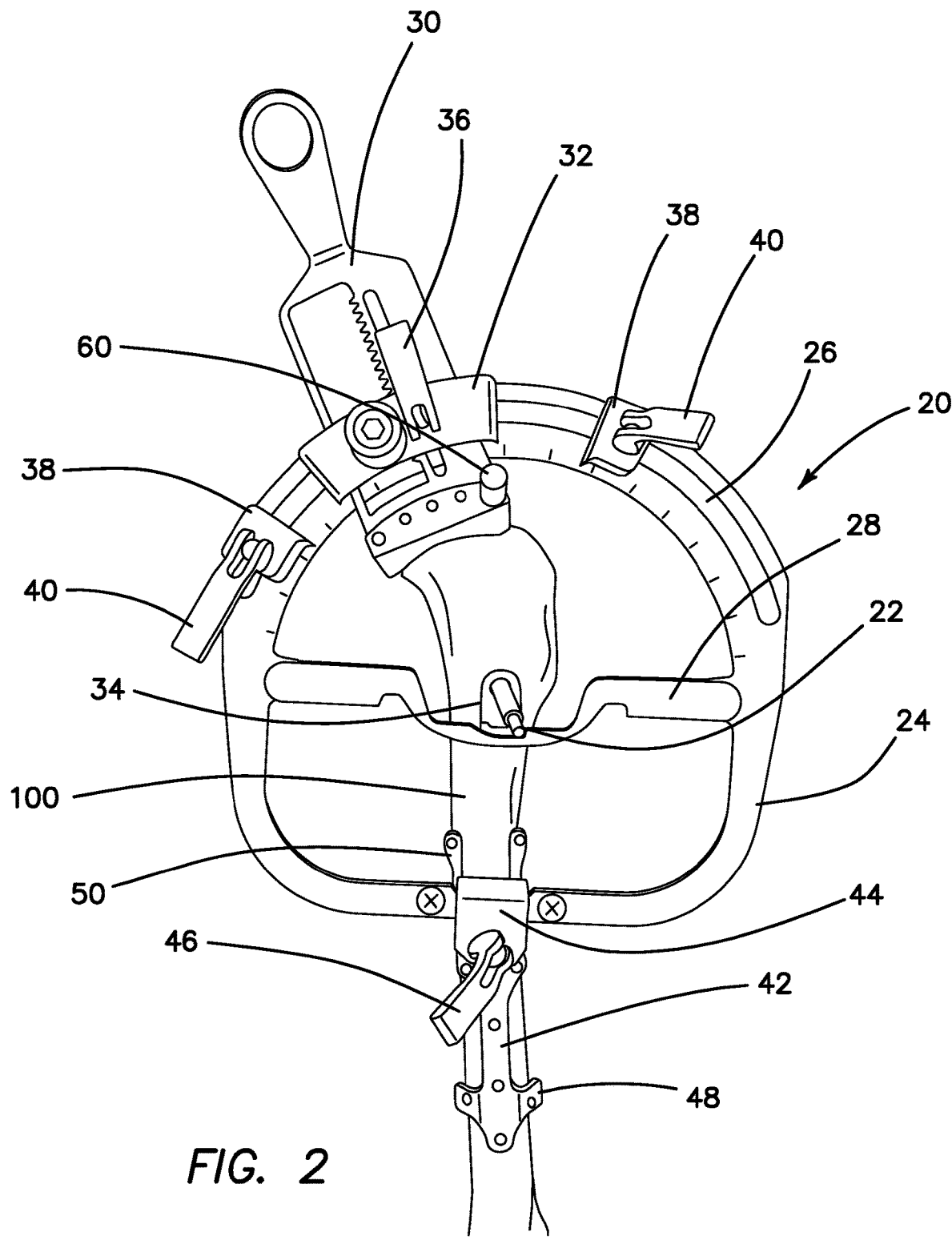
FIG. 2 is a top down view of the surgical guidance system (SGS) of the current invention when placed over the tibia of a canine.

Greater detail of the jig 20 may be seen by turning to FIG. 2 where it may be seen that the jig 20 comprises a frame 24 with an angular track 26 defined in a proximal end thereof. Disposed across a middle portion of the frame 24 is a bridge 28 which itself comprises a plate 34 configured to accommodate the centering pin 22 therein. Disposed in the angular track 26 is an angular tracking block 32 which may be slid throughout the length of the angular track 26. Within the angular tracking block 32 is a rotational handle 30 which may be moved radially inward and outward relative to a center portion of the frame 24 and then locked into position relative to the angular tracking block 32 via a proximal locking cam 36. Disposed on a distal end of the rotational handle 30 is a fixation block 58 which makes selective contact with the tibia 100 and a multiplanar plate 80 as is discussed in further detail below. The proximal locking cam 36 also fixes or locks the angular tracking block 32 into place relative to the angular track 26 when actuated. Also disposed in the angular track 26 on either side of the angular tracking block 32 are a pair of track guides 38, each comprising a corresponding a track cam lock 40.

Disposed at a distal portion of the frame 24 as seen in FIG. 2 is a lower arm 42 which is rotationally coupled to the frame 24 through a rotation block 44. The lower arm 42 may be adjusted by rotating the lower arm 42 relative to the frame 24 and then locked into a desired position by actuation of an arm cam lock 46. Disposed at a distal end of the lower arm 42 are a pair of contact feet 48 which are shaped to interact with the surface of the tibia 100 as is further detailed below. The lower arm 20 quickly and securely orients with the tibial shaft with mild digital pressure applied.

FIG. 2 further shows a substantially "U" or horseshoe shaped foot 50 is disposed on the lower arm 42 which extends into a center portion of the frame 24. Each prong of the foot 50 is specifically shaped to interact with the surface of the tibia 100 and provide additional support for the jig 20 while also avoiding interference with the multiplanar plate 80.

Figure 3A:
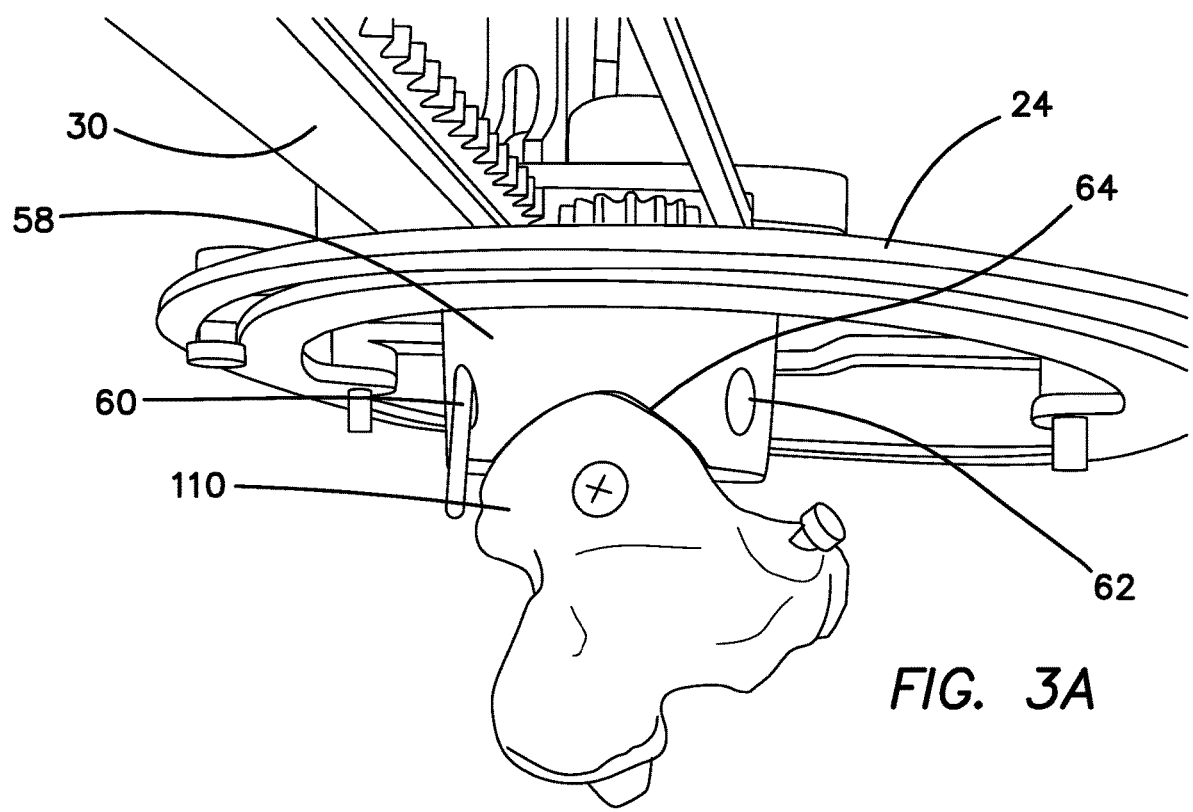
FIG. 3A is a distal end view of the SGS disposed over the tibia seen in FIG. 2, specifically with a concave surface of the fixation block portion of the jig disposed over the proximal portion of the tibia.
Figure 3B:
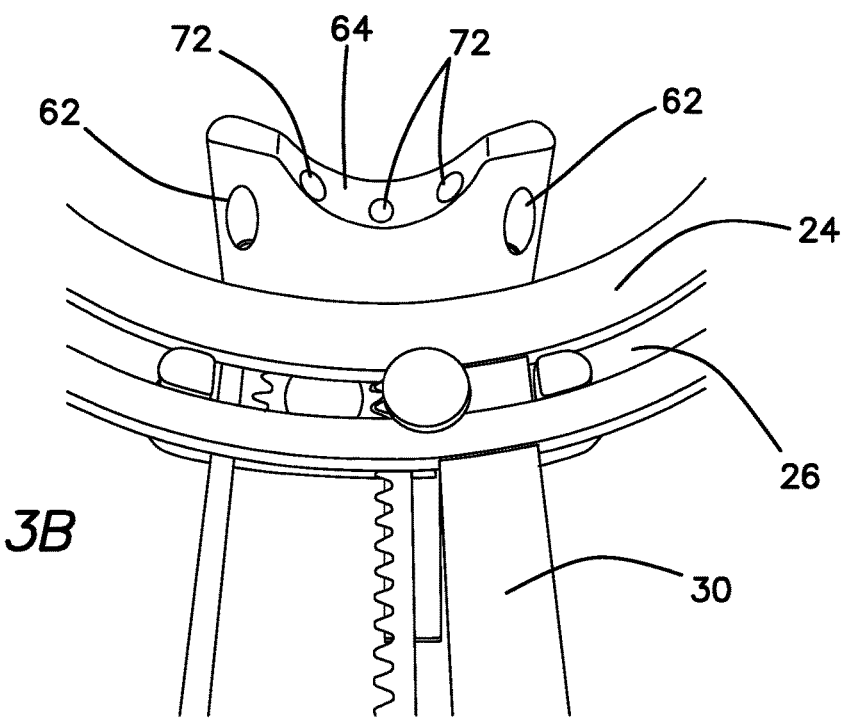
FIG. 3B is an inverted view of the concave surface of the fixation block portion of the jig seen in FIG. 3A.

The guide 10 and positioning jig 20 are utilized together for precise placement and guidance of the osteotomy 108, specific measurement of rotation, compression of the osteotomy, and specific implant placement. Once the intended position is identified, a centering pin 22 is placed and the guide 10 is removed. The centering pin 22 is placed perpendicular to the sagittal axis into the medial surface of the tibia 100. The jig 20 is then applied by sliding an aperture defined in the plate 34 over the centering pin 22 using the specifically designed bridge 28. All adjustment cam locks 36, 40, 46 are maintained in the released configuration to allow free movement of the jig 20. A contact surface 64 of the fixation block 58 of the jig 20 is substantially concave and apposes well with the proximal cortical surface of the tibia 100 as best seen in FIGS. 3A and 3B.

Figure 4:
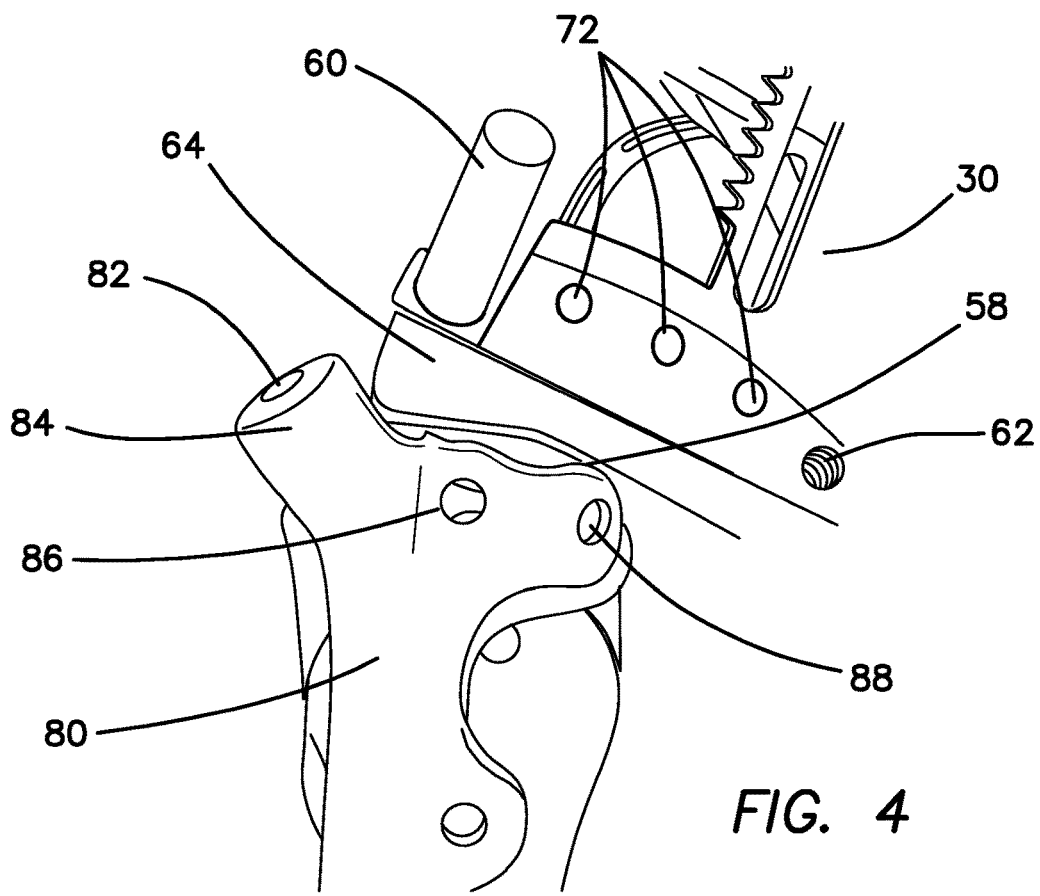
FIG. 4 is a magnified view of the interaction between the fixation block portion of the jig and the plate of the SGS.
Figure 8:
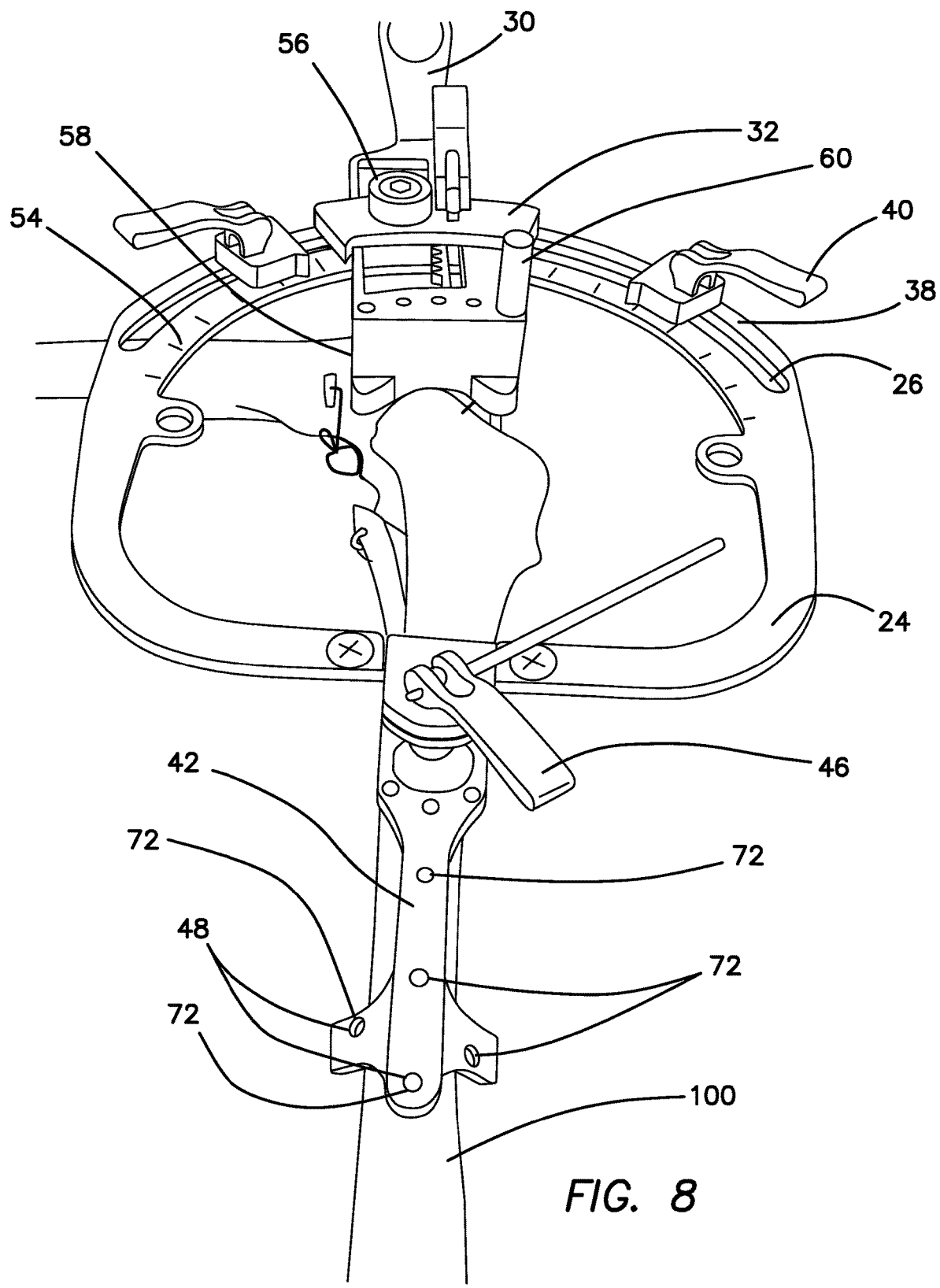
FIG. 8 is top perspective view of the jig after being placed on the tibia including a lower arm which is placed over the proximal length of the tibia.
Figure 12A:
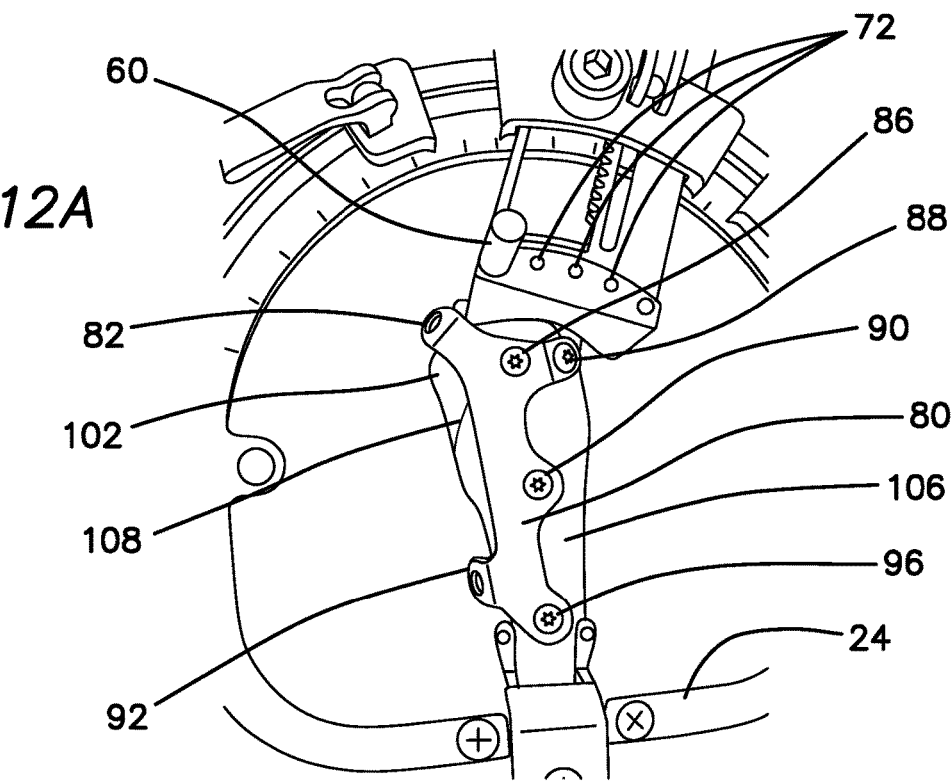
FIG. 12A is a top down view of the jig and plate being used to perform a pivot cruciate osteotomy on the left stifle of a canine.
Figure 12B:
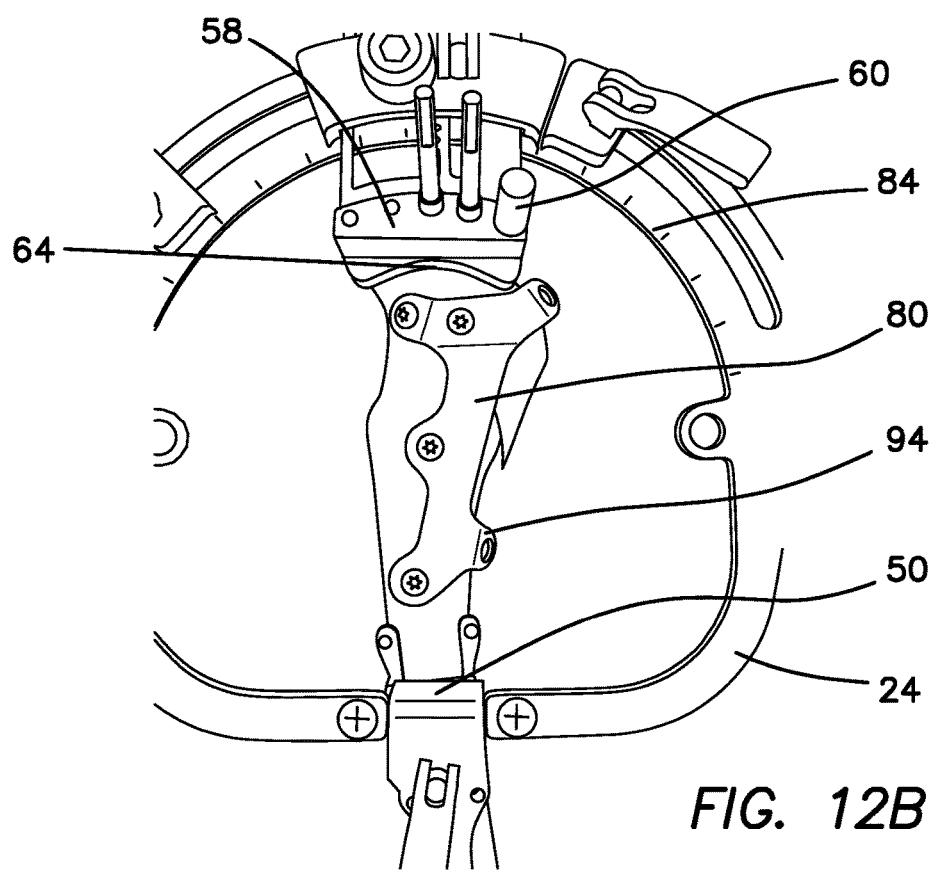
FIG. 12B is a top down view of the jig and plate being used to perform a pivot cruciate osteotomy on the right stifle of a canine.

A joint probe 60 is disposed through one of a plurality of apertures 62 defined in the fixation block 58 so that a distal end or tip of the joint probe 60 makes direct contact with the articular surface of the tibia 100, specifically in the region of the caudal infrapatellar fat pad. The joint probe 60 is inserted into the aperture 62 and then threadably engaged with a female thread defined within the apertures 62. The joint probe 60 is always inserted into the most cranially disposed aperture 62 defined within the fixation block 58. The relative position of the joint probe 62 is therefore dependent on which leg of the canine is currently undergoing the cruciate pivot osteotomy. For example, as seen in FIGS. 2 and 8, when the right hind leg of the canine is undergoing cruciate pivot osteotomy, the joint probe 60 is inserted into a right most disposed aperture 62. Conversely, as seen in FIGS. 4 and 12A, when the left hind leg of the canine is undergoing cruciate pivot osteotomy, the joint probe 60 is inserted into a left most disposed aperture 62. In other words, the joint probe 60 is to be placed in the cranial aspect of the joint, therefore for a right stifle, the joint probe 60 is placed in the right side of the fixation block 58, and vice versa. The joint probe 60 disposed through the fixation block 58 and the contact surface 64 of the jig 20 itself help to self-center the jig 20 into a very specific location. This provides very consistent placement of the jig 20 relative to the tibia 100 which is selectively locked into position once placed. The jig 20 is securely attached to the tibia through a plurality of quick connect fixation pins.

As best seen in FIG. 8, the lower arm 42 is placed over the tibia 100 and provides consistent tibia 100 positioning with smooth percutaneous pin placements in the arm 42 itself as well as in the feet 48, thereby preventing the need for the incision to be extended. Specifically, the lower arm 42 aligns itself with the tibia 100 by squeezing the lower arm 42 against the tibia 100.

Figure 15:
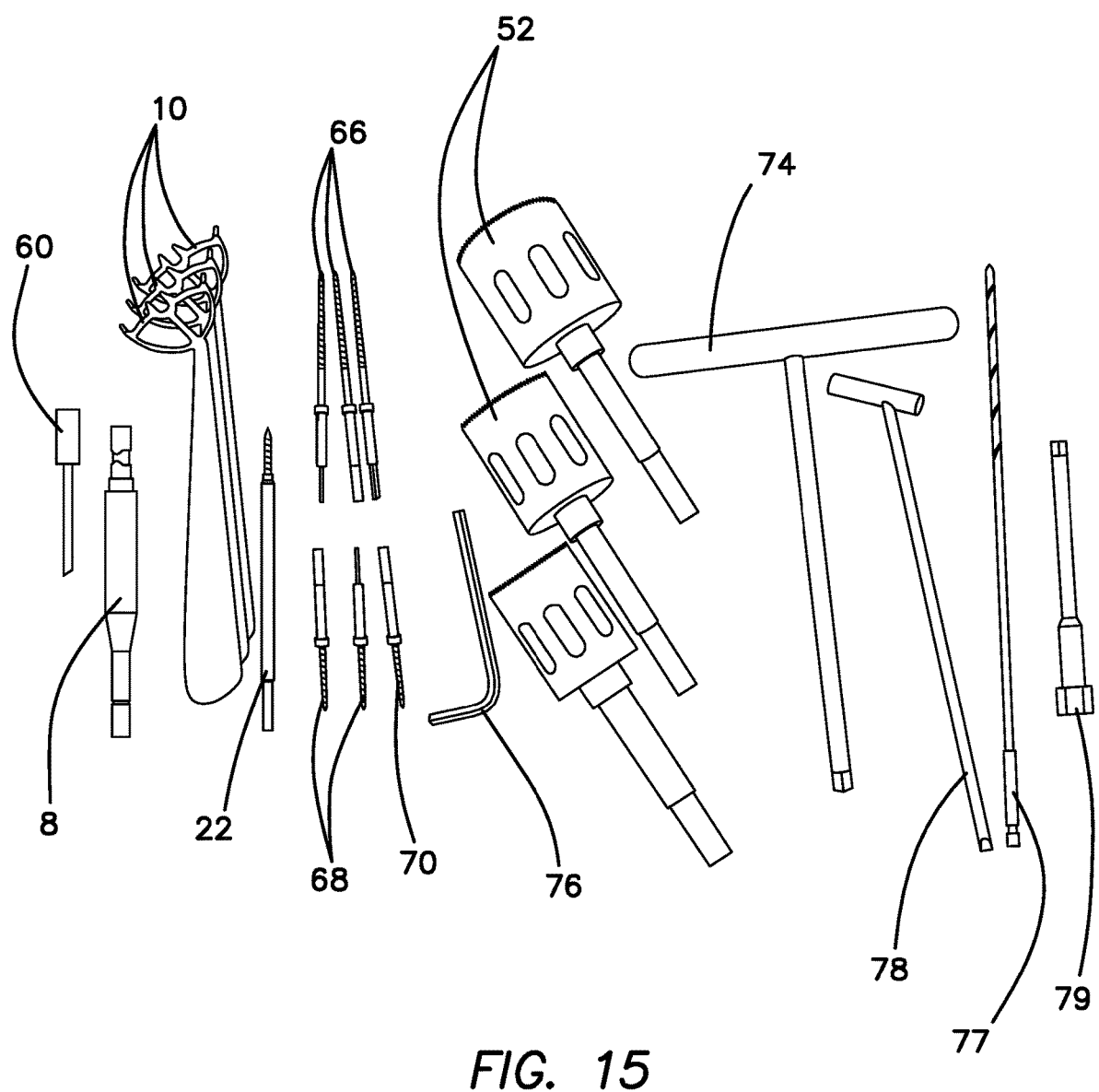
FIG. 15 is a top down view of a plurality instruments which are part of the SGS and which are used to perform the cruciate pivot osteotomy of the current invention.

Quick contact fixation pins 66, 68, 70 (seen in FIG. 15) are then be placed through a corresponding plurality of anchor sites 72 defined in the main portion of the lower arm 42, the fixation block 58, and the feet 48 with a power drill using a drill socket attachment. The proximal pins 66 which are preferably long threaded fixation pins are placed first by confirming the proximal attachment site location while being sure that the joint probe 60 is slid caudally away from the patella tendon. Next a plurality of distal pins 68 and a smooth fixation pin 70 which are preferably short threaded fixation pins and a percutaneous anchor, respectively, are inserted into the anchor sites 72. Typically, two to three pins 66, 68 are placed in both the fixation block 58 and the lower arm 20. Prior to pin placement, the jig 20 typically is stable and conforms well with the tibia 100 both proximally and distally. Once the jig 20 is secured, the lower arm 42 is then secured by locking the lower arm 42 into place relative to the frame 24 of the jig 20 by actuation of the arm cam lock 46, thereby preventing sagittal translation. The lower arm 42 makes performance of the cruciate pivot osteotomy of the current invention easier by making placement and anchorage of the jig 20 to the tibia 100 much simpler and with better consistency of measurement.

Figure 9:
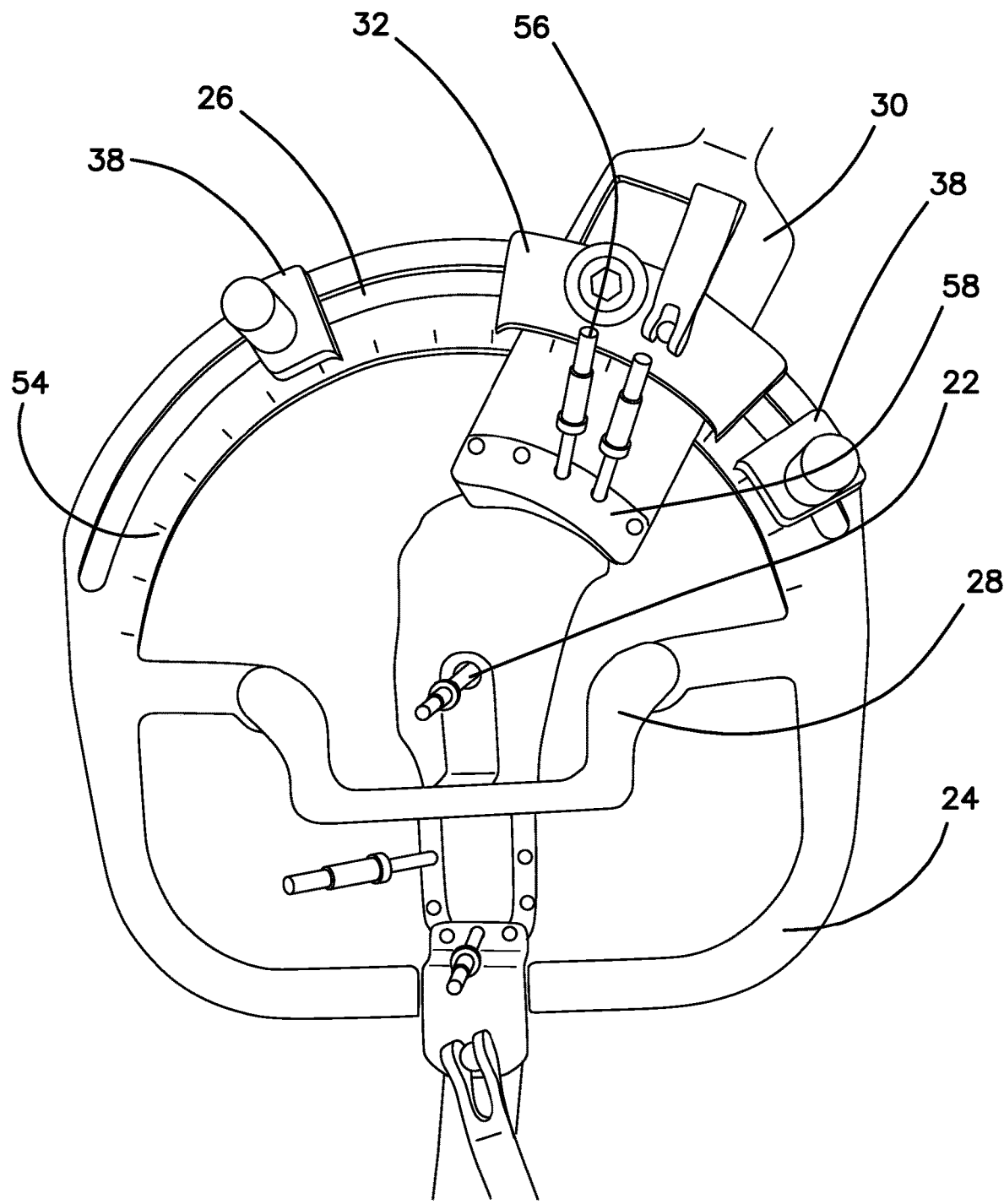
FIG. 9 is a top down view of the jig placed on the tibia, specifically before the fixation block and rotation handle have rotated the distal portion of the tibia forward.
Figure 10:
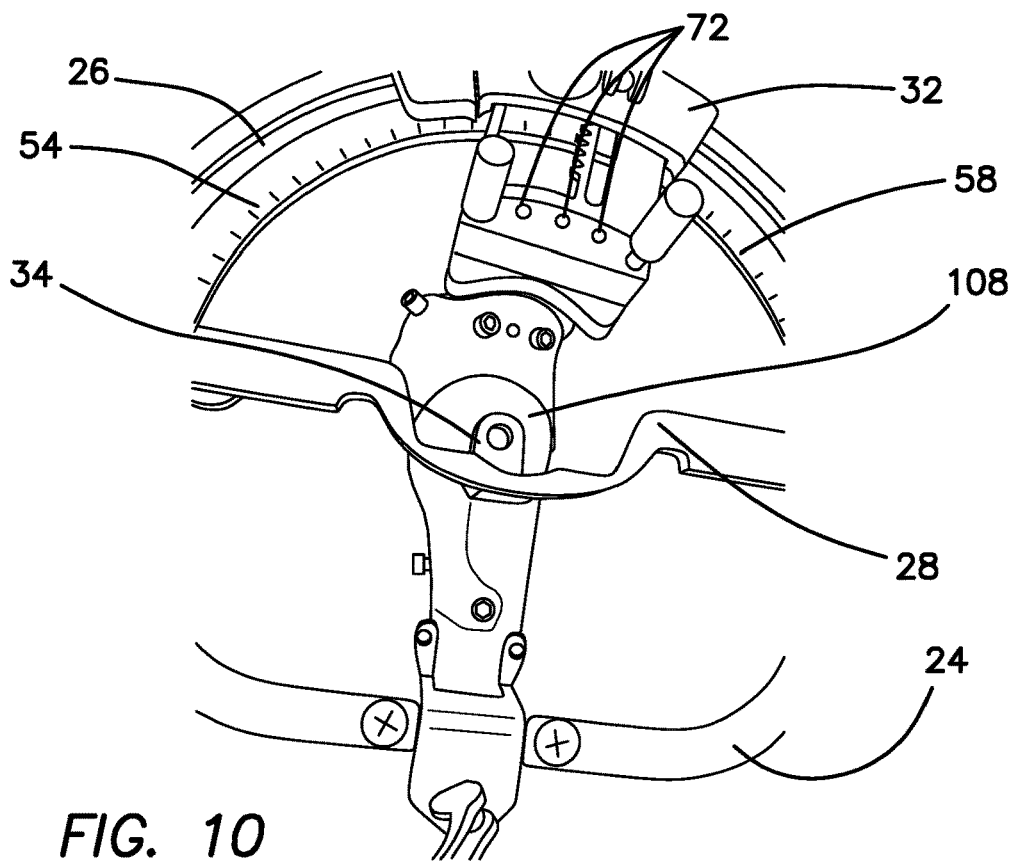
FIG. 10 is a top down view of the jig seen in FIG. 9 after the fixation block and rotation handle have rotated the distal portion of the tibia forward.

The desired rotational angle of the proximal tibia 102 can be preset while also preserving the original starting angle. In other words, both the starting and the desired final rotational positions are identified and then the jig 20 can be set so that the rotational handle 30 and angular tracking block 32 can only be rotated between those two predefined positions. The user may manipulate the two track guides 38 disposed in the frame 24, specifically within the semi-circular or angular track 26 defined in the frame 24 seen in FIGS. 8 and 9. The angular track 26 comprises a scale 54 printed or otherwise disposed on its surface so that the user can set each of the track guides 38 to their respective desired angles by being slid through the aperture defining the angular track 26. Once at the desired angular position within the angular track 26, each track guide 38 is locked into position via its corresponding track cam lock 40, thus providing the desired rotational displacement and identifying the pre-surgical angle, desired post-surgical angle, and the corrective displacement angle disposed there between. The scale 54 is easily legible and negates the need to place bone markers. Additional verification is not needed, but it can be provided if desired by placing a mark on each side of the osteotomy 108 and measuring the displacement which provides the chord. A standard TPLO chart can then be used. Additionally, the fixation block 58 disposed on an end of the rotational handle 30 may be brought up against the proximal tibia 102 by actuation of a compression screw 56 disposed through the angular tracking block 32 with a T handle 74 (seen in FIG. 15) which moves the rotational handle 30 radially inward relative to the frame 24 of the jig 20 as is known in the art.

After proper positioning, the jig 20 is then used to allow exact placement of the osteotomy 108. The location of the osteotomy 108 is automatically determined according to the location of the positioning guides disposed on the jig 20. In other words, after the jig 20 has been placed over the centering pin 22 as disclosed above, the positioning guides of jig 20 interact with the specific anatomical features of the tibia 100 so as to quickly and accurately orientate the jig 20 for performing the cruciate pivot osteotomy procedure. An osteotomy blade 52 is disposed over or threaded by the centering pin 22 as seen in FIGS. 2 and 3 and then confirmed for being the proper size for the canine undergoing the cruciate pivot osteotomy procedure, namely the osteotomy should exit nearly parallel to the cortical surface. The osteotomy blade 52 is precisely three-dimensionally constrained in orientation providing a very exact osteotomy 108. The blade portion may be further tightened to the housing of the osteotomy blade 52 with an Allen wrench 76 (seen in FIG. 15). The osteotomy can be performed in one maneuver by rotating the osteotomy blade 52 about the centering pin 22 while being fully submerged in cool saline to diminish heat generation at the osteotomy 108 and lubricate the cutting action as visualization of the osteotomy 108 is not required. The osteotomy blade 52 is cannulated and provides a defined three-dimensional orientation. The osteotomy blade 52 is also bi-radial which provides circumferential compression post rotation and ideal three-dimensional apposition. Because of this, the resulting osteotomy 108 has full three-dimensional guidance and is much easier to create than a TPLO osteotomy. The user can feel completion of the osteotomy 108 as the blade tone changes and the resistance diminishes. Completion of the osteotomy 108 can typically be felt while making the cut, but it can also be verified by using the rotational handle 30 to distract the osteotomy 108 and confirm the completion of the osteotomy 108 and reduce soft tissue interference during rotation.

It should be noted that the medial surface of the tibia 100 is not uniform nor is it perfectly perpendicular to the sagittal plane of the tibia, thus blade contact with the bone is problematic with a non-guided blade. Accurate placement of the osteotomy 108 is challenging as the blade vibrates and jumps when performing with a rotary oscillating saw blade. The centering pin 22 has been developed to cannulate the osteotomy blade 52 which locks into the frame 24 to ensure a circular osteotomy 108 as opposed to a more irregular cut or elliptical cut which easily occur without guidance (or a "free-hand" approach). The osteotomy 108 resulting from the current cruciate pivot osteotomy is longer than a TPLO osteotomy and approaches 180 degrees. The osteotomy blade 52 comprises a longer cutting surface which is proportional to the length of required osteotomy. In one preferred embodiment, the cutting depth of the osteotomy blade 52 is 30 mm that is acceptable for nearly all dog breeds, with the exception of larger breed dogs who have a tibial thickness ranging about 15-25 mm.

Following completion of the osteotomy 108, the proximal tibia 102 is easily rotated using the track guides 38 to mark the desired rotation angle. Specifically, the rotational handle 30 which is preferably initially adjacently disposed next to the most caudally disposed track guide 38 is gripped by the user and then rotated in the cranial direction until meeting the opposing or most cranially disposed track guide 38. Once fully rotated to the desired angular position, the rotational handle 30 and angular tracking block 32 are locked into place through actuation of the proximal locking cam 36, thereby also fixing the proximal tibia 102 into its new desired angular orientation relative to the distal tibia 106.

The rotational handle 30 is then used to compress the osteotomy 108 by further actuation of the compression screw 56 disposed through the angular tracking block 32 which presses the fixation block 58 further against the proximal tibia 102, thereby providing complete apposition and compression across the osteotomy 108. After the compression screw 56 has been adjusted, the jig 20 is then completely locked which stabilizes the rotational and compressive forces being exerted onto the proximal tibia 102. Readjusting the rotation of the proximal tibia 102 is easily made by loosening the proximal locking cam 36, readjusting the rotational handle 30 and/or frame 24, and then once again fixing the rotational handle 30 into place by tightening the proximal locking cam 36. Precise, accurate and easily measured rotation of the proximal tibia 102 is provided by the scale 54 disposed directly adjacent to the angular track 26.

Next, the bridge 28 coupled to the frame 24 is removed along with the centering pin 22 to provide full, unobstructed access to the medial surface of the tibia 100 and allow for correct placement of the multiplanar plate 80 as seen in FIGS. 10-13. The joint probe 60 is removed by being unscrewed prior to the placement of the multiplanar plate 80 as the cranial arms 84, 94 of the multiplanar plate 80 slide into this specific position.

Turning to FIGS. 10-12B, the multiplanar plate 80 is placed using the jig 20 to guide its placement. The jig 20 provides specific screw offset which results in consistent screw placement and diminishes the risk of joint penetration. The multiplanar plate 80 used to perform the cruciate pivotal osteotomy of the current invention is pre-contoured or predefined to fit the medial tibial surface so as to make placement of the multiplanar plate 80 as simple as possible. Specifically, the multiplanar plate 80 is slid against the cranial surface 110 of the proximal tibia 102 until a proximal cranial arm 84 and a distal cranial arm 94 of the multiplanar plate 80 are in good contact against the cranial surface of the proximal tibia 102 and the distal tibia 106, respectively. Additionally, the proximal cranial arm 84 of the multiplanar plate 80 is placed so as to make contact with a cranial edge or portion of the fixation block 58 as best seen in FIG. 4. It is important to note that a corresponding first and second cranial screw site 82, 92 defined in the proximal cranial arm 84 and the distal cranial arm 94 of the multiplanar plate 80 are in contact with the cranial surface of the tibia 100 at their respective locations. Additionally, both the proximal cranial arm 84 and the distal cranial arm 94 wrap around the cranial aspect of the cranial tibia 102 and distal tibia 106, where it becomes extremely easy to apply or implement a plurality of bone screws since the tibia 100 becomes relatively broad and flat at those locations. Note that the joint probe 60 will interfere with the position of the multiplanar plate 80 if not removed by this point in the procedure.

The multiplanar plate 80 provides at least six screw sites to provide ideal placement and orientation, namely first and second cranial screw sites 82, 92 as discussed above, as well as first, second, third, and fourth medial screw sites 86, 88, 90, 96. A screw is first placed through the first medial screw site 86 to confirm good apposition of the multiplanar plate 80 followed by additional screws being inserted through the third, second, and fourth medial screw sites 90, 88, 96. The osteotomy 108 is stable at this point, allowing for removal of the jig 20 completely and placement of additional screws through the first and second cranial screw sites 82, 92. No additional contouring of the multiplanar plate 80 is required since contact is emphasized at the screw-bone interface, but the rest of the multiplanar plate 80 remains slightly raised relative to surface of the bone. For example, first cranial screw sight 82, first medial screw site 86, second medial screw site 88, second cranial screw site 92, and fourth medial screw site 96 are securely contacting bone, thereby making the multiplanar plate 80 "hug" or remain close the surface of the bone at those specific locations. The material comprising the multiplanar plate 80 around each screw site is raised so that it is preferably in contact with the bone for a 2-3 mm circumference around each screw site. The close approximation of the surrounding multiplanar plate 80 and the cortical surface further stabilizes the locking screw interface by diminishing the shear forces across the proximal screw region and screw-plate interface. The close approximation of the multiplanar plate 80 and the cortical surface also nearly eliminates micro motion since the multiplanar plate 80 is abutted directly onto the interface of the bone which also comprises multiplanar fixation.

It should be noted that inserting a screw into each of the screw sites 82, 86, 88, 90, 92, 96 is easy to perform. Each screw is inserted into its respective screw site by first placing a drill guide 78 (seen in FIG. 15) into the screw site and then drilling a guide hole with a 2.8 mm drill bit 77 (seen in FIG. 15) attached to a power drill. Next a power star driver 79 (also seen in FIG. 15) attached to a power drill may be used to drive each screw into the screw site. The first cranial screw site 82 in particular is disposed at a very easy location in which to implement a bone screw. The orientation of the first cranial screw site 82 is very specific to this specific region of the tibia 100, thereby providing customized bone purchase and stability and yet reasonably uniformity between patients. The first cranial screw site 82 is 70-75 degrees relative to the orientation of the multiplanar plate 80 and is slightly medial which results in a multiplanar plate 80 that is much easier to control during performance of the cruciate pivot osteotomy procedure since it therefore also avoids tendon interference. In addition, the multiplanar plate 80 is disposed on a more proximal portion of the tibia 100, resulting in the multiplanar plate 80 being disposed on thicker bone. This results in a large target caudally which, when combined with controlled cranial movement and a locking drill guide, makes the cruciate pivot osteotomy nearly impossible to place incorrectly. Furthermore, the first and second cranial screw sites 82, 92 work like a locking "hook plate" and therefore provide additional resistance to rotational movement.

In summary, the multiplanar plate 80 is a smooth press fit locking screw-plate interface. The smooth interface provides very consistent and reasonably rigid screw-plate rigidity without concern of miss threading, cross threading, or incorrect threading which occur with incorrect angulation or off rotation in threaded systems. The non-threaded interface ensures compression of the low contact pegs with the bone surface providing better multi-contact fixation. The plate pegs are also driven into engagement into the cortical bone of the tibia. Thus the screw site fixation comprises the screw-plate plus the base of several pegs contacting the cortical surface. The screws are oriented in convergence so that it is not dependent on screw purchase but on screw orientation geometry. Furthermore, the design of the multiplanar plate 80 provides a specific screw orientation geometry specifically for the proximal tibia. Specifically, the multiplanar plate 80 specifically counteracts cranial tension forces and torsional forces providing weight-bearing three-dimensional rigidity.

Figure 11:
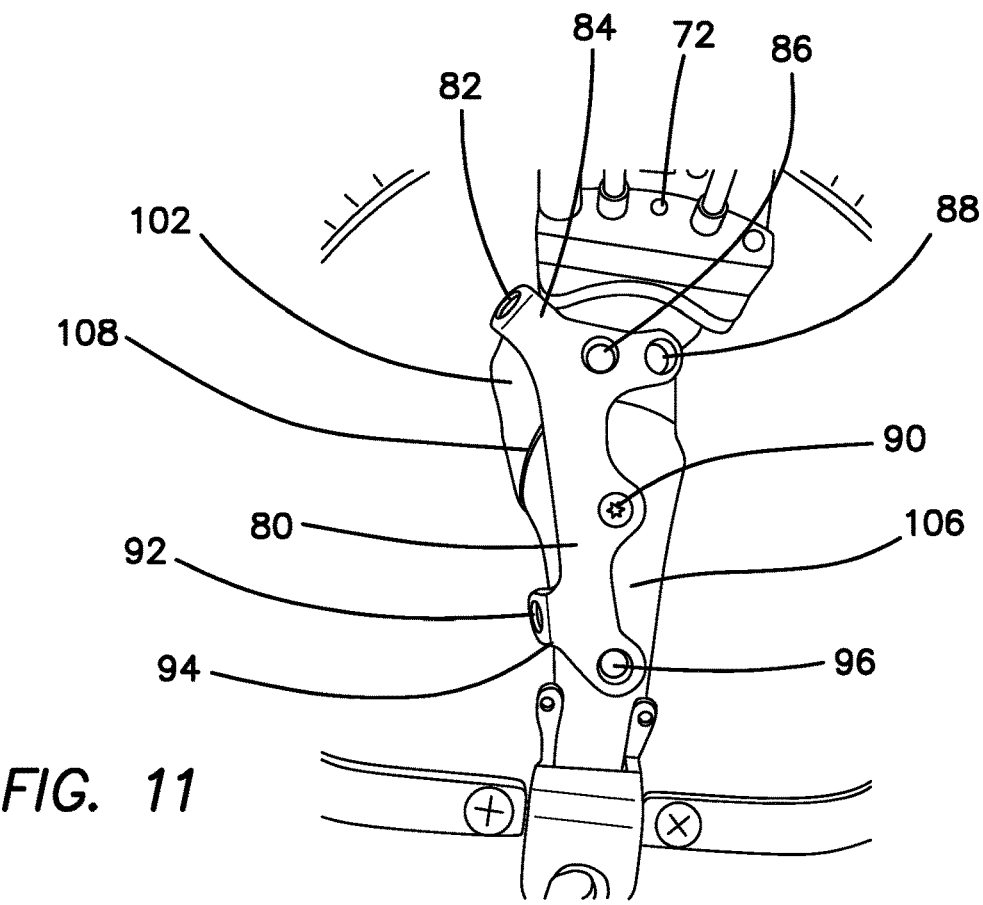
FIG. 11 is a top down view of the jig seen in FIG. 10 after a bridge portion of the jig has been removed and after a plate has been placed over the osteotomy.
Figure 13:
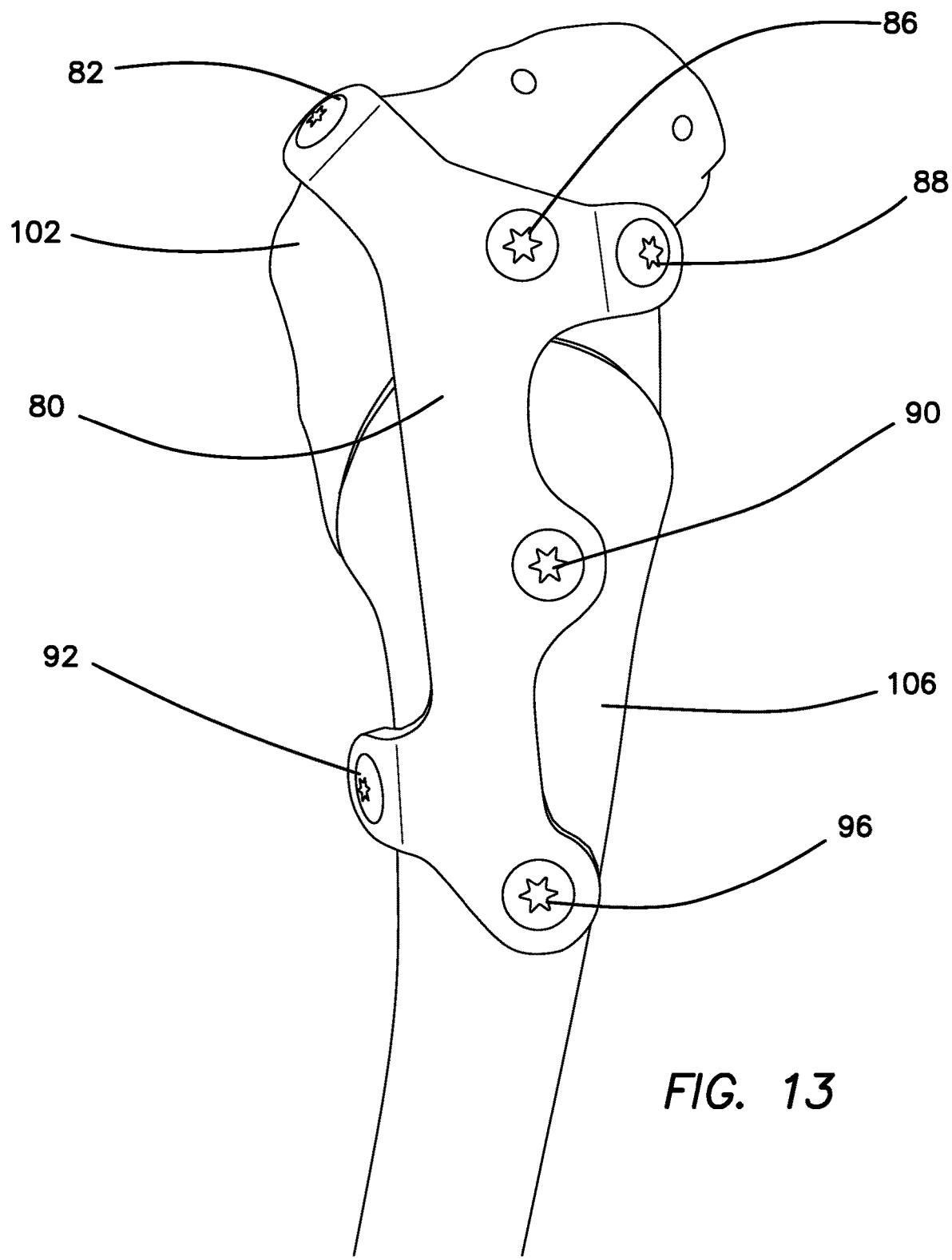
FIG. 13 is magnified top down view of the plate after being fully implanted to the tibia and after the jig has been removed from the surgical site.

The specific position and configuration of the jig 20 determines the position of the multiplanar plate 80 relative to the osteotomy 108. The multiplanar plate 80 as seen in FIGS. 11-13 pushes a screw disposed through the first or second medial screw sites 86, 88 towards the osteotomy 108. The multiplanar plate 80 may further comprise a small indentation which provides a "key and lock" fit when combined with the jig 20.

The entire operation site is lavaged with sterile saline. Any additional procedures and a standard closure of the site can be performed in a three-layer manner (medial retinaculum, subcutaneous tissues and skin) as is known in the art.

Figure 14A:
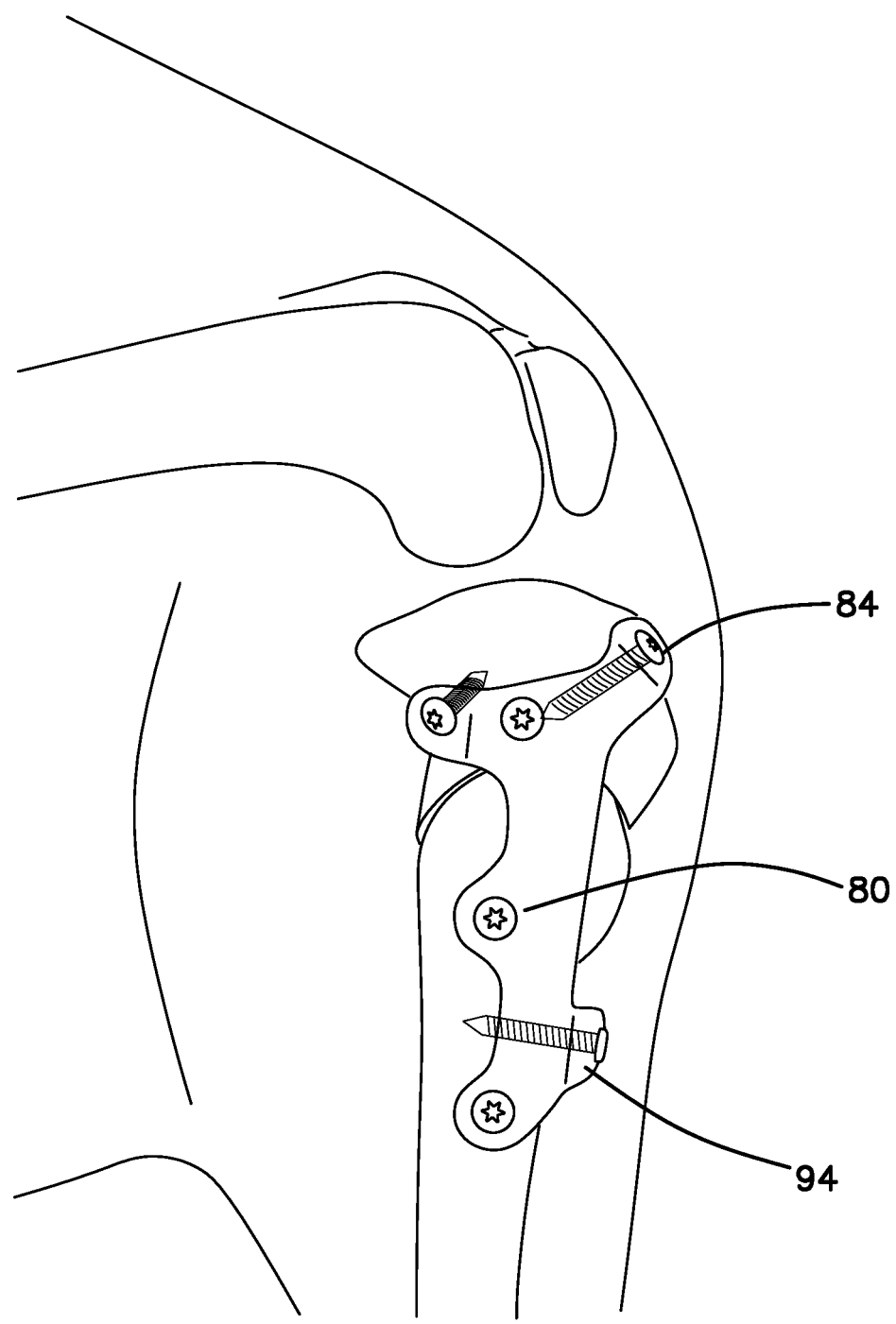
FIG. 14A is a side x-ray view of a stifle of a canine after the plate has been implanted using a plurality of bone screws.
Figure 14B:
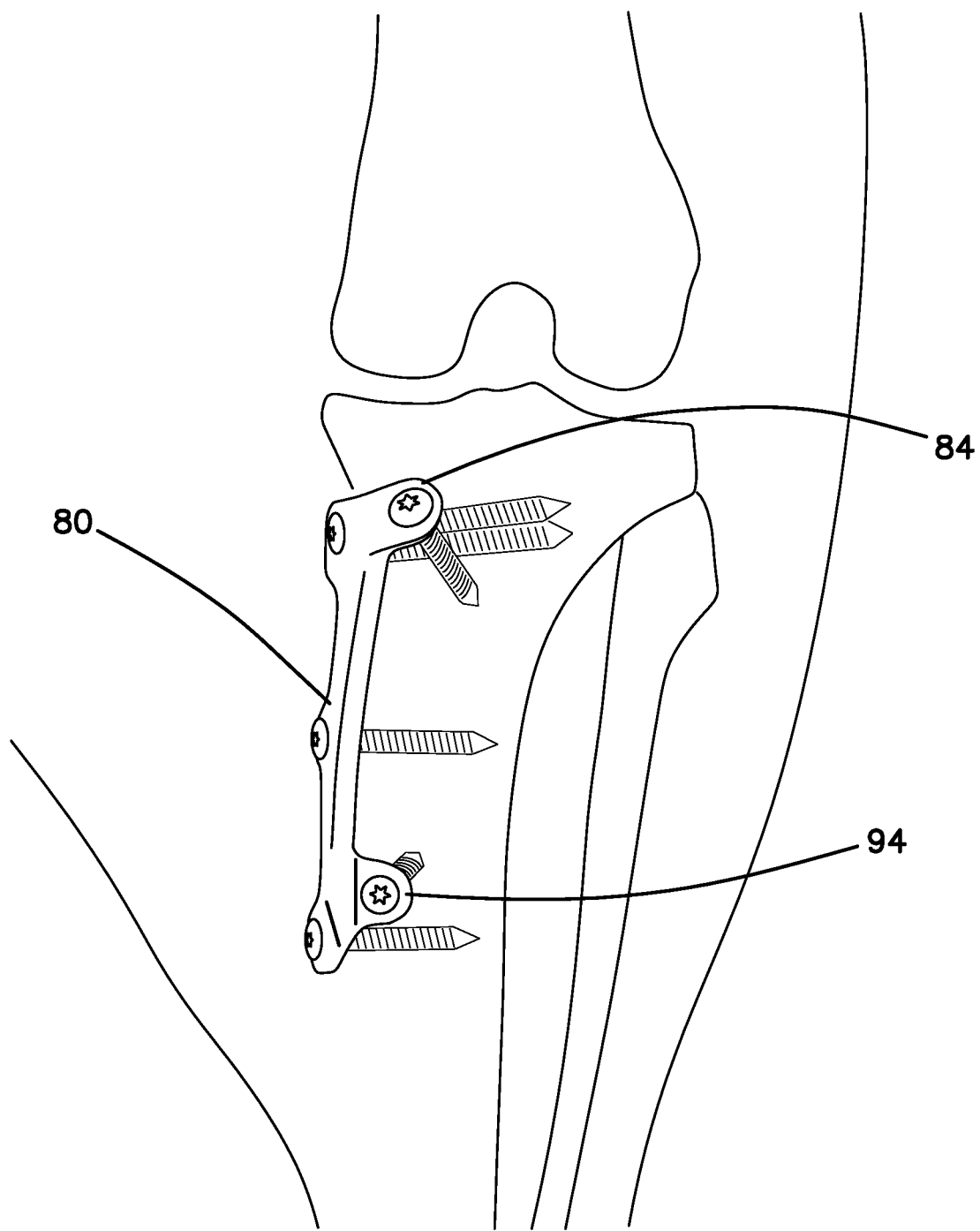
FIG. 14B is a cranial x-ray view the stifle of the canine seen in FIG. 14A.

Post-operative radiographs are performed as seen in FIGS. 14A and 14B with evaluation of tibial plateau angle, patella tendon angle, mechanical axis, implants and cranial tibial tuberosity translation. A harness can be used so that the canine can walk immediately with high mobility and with minor assistance. Most patients can begin to bear weight on the leg within a few days of the procedure. Comfort is optimized in early recovery with multimodal medications during the first two weeks. Incisional and regional soft tissues heal quickly with suture removal at two weeks. Progressive increases in weight bearing occur quickly over weeks with rapid rebuilding muscle strength and mass. Additionally, a progressive increase in controlled activity is recommended with inclusion of specifically designed exercises and activities to accelerate recovery. These activities are varied and often reported as a fun experience by owners and of course the canines who love the attention. Patients ordinarily graduate to complete full activity with no restrictions between 12-16 weeks following surgery. Return to full activity without restriction is expected.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments include other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. A method for treating cruciate ligament disease comprising:
    determining an insertion position on a tibia with a guide;
    inserting a centering pin at the determined insertion position on the tibia;
    disposing a jig comprising a frame and an adjustable angular tracking block disposed within an angular track defined within the frame onto the tibia;
    defining an osteotomy in the tibia;
    rotating a proximal portion of the tibia by rotating a rotational handle disposed on the angular tracking block;
    securing the proximal portion of the tibia into a post-rotational position by actuating a locking cam configured to selectively lock the angular tracking block to a selected position within the angular track; and disposing a plate in a position over the osteotomy as determined by the frame of the jig.

2. The method of claim 1 wherein determining the insertion position on the tibia for a centering pin with the guide comprises:

disposing a first positioning peg coupled the guide adjacent to a cranial surface of the tibia; and disposing a second positioning peg coupled on the guide adjacent a caudal surface of the tibia, wherein disposing the first and second positioning pegs adjacent to the cranial and caudal surfaces of the tibia respectively automatically centers a notch defined within the guide over the insertion position on the tibia for the centering pin.

3. The method of claim 1 wherein disposing the jig comprising a frame and an adjustable angular tracking block disposed within an angular track defined within the frame over the tibia comprises aligning at least one joint probe coupled to an adjustable fixation block disposed on a distal end of the rotational handle with at least one anatomical feature of the tibia.

4. The method of claim 3 wherein disposing the jig comprising a frame and an adjustable angular tracking block disposed within an angular track defined within the frame onto the tibia comprises aligning a concave surface of the adjustable fixation block with a corresponding convex surface of a proximal portion of the tibia.

5. The method of claim 1 wherein disposing the jig comprising a frame and an adjustable angular tracking block disposed within an angular track defined within the frame over the tibia comprises:

disposing a lower arm rotationally coupled to the jig over the length of a distal portion of the tibia; and locking the lower arm into a fixed position relative to the jig and to the distal portion of the tibia.

6. The method of claim 5 wherein locking the lower arm into a fixed position relative to the jig and to the distal portion of the tibia comprises aligning a plurality of feet disposed on the lower arm with a cranial and a caudal surface of the distal portion of the tibia.

7. The method of claim 1 wherein disposing the plate in a position over the osteotomy as determined by the frame of the jig comprises inserting the plate within a center of the frame of the jig.

8. The method of claim 1 wherein disposing the plate in a position over the osteotomy as determined by the frame of the jig comprises disposing at least two cranial arms of the plate on a cranial surface of the tibia.

9. The method of claim 8 wherein disposing at least two cranial arms of the plate on a cranial surface of the tibia comprises disposing one of the at least two cranial arms of the plate on a proximal cranial surface of the tibia and disposing one of the at least two cranial arms of the plate on a distal cranial surface of the tibia.

10. The method of claim 1 wherein rotating the proximal portion of the tibia by rotating the rotational handle disposed on the angular tracking block comprises rotating the proximal portion of the tibia through a rotation angle defined between a plurality of adjustable track guides disposed within the angular track.

11. The method of claim 10 wherein rotating the proximal portion of the tibia through a rotation angle defined between a plurality of adjustable track guides disposed within the angular track comprises sliding the rotational handle disposed on the angular tracking block through the angular track defined within the frame of the jig until contacting at least one of the plurality of track guides.

12. The method of claim 11 wherein disposing the plate in a position over the osteotomy as determined by the frame of the jig comprises aligning the plate with the rotational handle after it has made contact with the at least one of the plurality of track guides.

13. The method of claim 1 wherein determining the insertion position on a tibia with the guide further comprises obtaining a visual indication of the position of the osteotomy to be defined in the tibia.

14. A system for treating cruciate ligament disease comprising:

a removable guide;

an adjustable jig; and a multiplanar plate configured to be inserted through a frame of the jig and onto a tibia, wherein the jig comprises an adjustable angular tracking block disposed within an angular track defined within the frame of the jig, wherein the angular tracking block comprises:

a rotational handle comprising a distal end;

an adjustable fixation block disposed on the distal end of the rotational handle; and a locking cam configured to selectively lock the angular tracking block to a selected position within the angular track, wherein the angular track comprises a scale disposed on a surface of the angular track, and wherein the adjustable fixation block comprises at least one removable joint probe disposed therein which is configured to make direct contact with an articular surface of the tibia.

15. The system of claim 14 wherein the guide comprises a plurality of positioning pegs configured to interact with a cranial surface and a caudal surface of the tibia, respectively.

16. The system of claim 15 wherein the guide further comprises a notch defined between the plurality of positioning pegs.

17. The system of claim 14 wherein the jig comprises a lower arm rotationally coupled to the frame of the jig and configured to extend down a length of a distal portion of the tibia.

18. The system of claim 17 wherein the lower arm comprises a plurality of feet disposed on a distal end of the lower arm, the plurality of feet configured to contact a cranial surface and a caudal surface of the tibia, respectively.

19. The system of claim 14 wherein the multiplanar plate comprises a plurality a cranial arms configured to extend from a medial surface of the tibia and couple to a cranial surface of the tibia.

20. The system of claim 14 wherein the jig comprises:

a track guide disposed within the angular track on either side of the angular tracking block disposed within the track.

* * * * *